US012569577B2

(12) United States Patent
Huang

(10) Patent No.: US 12,569,577 B2
(45) Date of Patent: Mar. 10, 2026

(54) PSMA-TARGETING IMAGING AGENTS

(71) Applicant: The Cleveland Clinic Foundation, Cleveland, OH (US)

(72) Inventor: Steve Shih-lin Huang, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 956 days.

(21) Appl. No.: 17/770,382

(22) PCT Filed: Oct. 28, 2020

(86) PCT No.: PCT/US2020/057667

§ 371 (c)(1),
(2) Date: Apr. 20, 2022

(87) PCT Pub. No.: WO2021/086917

PCT Pub. Date: May 6, 2021

(65) Prior Publication Data

US 2023/0016265 A1 Jan. 19, 2023

Related U.S. Application Data

(60) Provisional application No. 62/927,185, filed on Oct. 29, 2019.

(51) Int. Cl.
*A61K 51/08* (2006.01)
*A61P 35/00* (2006.01)

(52) U.S. Cl.
CPC ............ *A61K 51/088* (2013.01); *A61P 35/00* (2018.01)

(58) Field of Classification Search
CPC ...... A61K 51/00; A61K 51/08; A61K 51/088; A61K 49/00; A61K 49/0002; A61K 38/00; A61K 49/0032; A61K 49/0043; A61K 49/0052; A61K 49/0056; A61K 51/04; A61K 51/0404; A61K 51/0497; A61P 35/00; C07B 2200/07; C07B 59/008; C07B 213/82; C07B 257/02; C07B 403/14; C07B 493/10; C07B 1/32; C07B 5/021; C07B 5/0819; C07B 5/1021
See application file for complete search history.

(56) References Cited

U.S. PATENT DOCUMENTS 9,713,649 B2 * 7/2017 Huang ............... A61K 49/0032
10,918,741 B2 * 2/2021 Huang ............... A61K 49/0032
2004/0001790 A1 * 1/2004 Hilger .................... C07K 16/18 424/1.69
2019/0298843 A1 10/2019 Low et al.

FOREIGN PATENT DOCUMENTS

WO 2019190266 A1 10/2019
WO 2019191728 A1 10/2019

OTHER PUBLICATIONS

Liu, et al.; Near-Infrared Neodymium Tag for Quantifying Targeted Biomarker and Counting Its Host Circulating Tumor Cells; Anal. Chem. 2017, 89, 17, pp. 9239-9246.
International Search Report and Written Opinion in PCT/US2020/057667; Mailing Date: Feb. 10, 2021.

* cited by examiner

*Primary Examiner* — D. L. Jones
(74) *Attorney, Agent, or Firm* — Tucker Ellis LLP

(57) ABSTRACT

A PSMA-specific agent comprising a compound according to Formula I or Formula II: wherein $S_1$ is absent or is an organic spacer group comprising 3-10 carbons; A is an amino acid chain comprising 1 to 5 amino acids wherein at least one of the amino acids is selected from glutamic acid and aspartic acid; S2 is absent or is an organic spacer group comprising 1 to 15 carbons and/or 0 to 2 amino acids; $I_1$ is an imaging group; and $I_2$ is absent or is an imaging group. The PSMA-specific agents can be used to image PSMA within a tissue region and/or for the treatment of a cancer, such as prostate cancer.

I

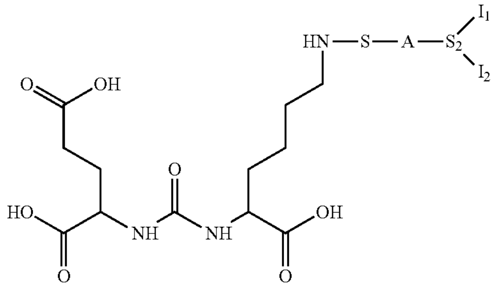

II

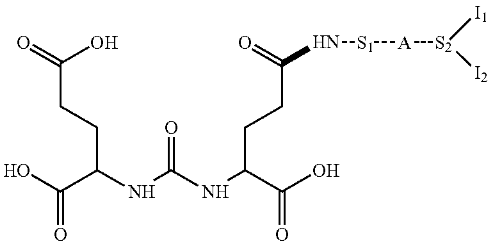

21 Claims, 6 Drawing Sheets

PSMA-TARGETING IMAGING AGENTS

RELATED APPLICATION

This application claims the benefit of U.S. Provisional Application No. 62/927,185 filed Oct. 29, 2019, which is hereby incorporated by reference in its entirety.

TECHNICAL FIELD

The disclosure relates to imaging and therapeutic agents that are specific for prostate specific membrane antigen (PSMA). The agents comprise a compound according to Formula I or Formula II:

I

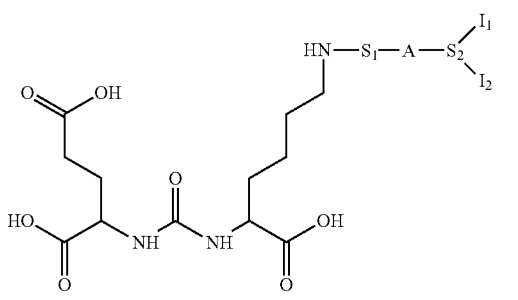

II

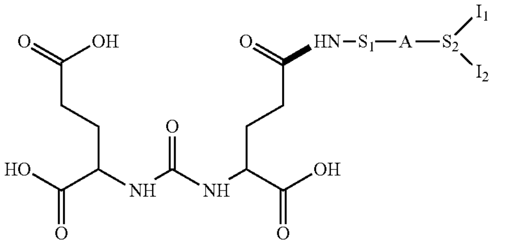

wherein $S_1$ is absent or is an organic spacer group comprising 3-10 carbons; A is an amino acid chain comprising 1 to 5 amino acids wherein at least one of the amino acids is selected from glutamic acid and aspartic acid; $S_2$ is absent or is an organic spacer group comprising 1 to 15 carbons and/or 0 to 2 amino acids; $I_1$ is a first imaging group; and $I_2$ is optionally a second imaging group. The PSMA-specific agents can be used to image PSMA within a tissue region to guide the treatment of diseases such as prostate cancer. The PSMA-specific agents can also be used as targeted therapeutics for the treatment of diseases such as prostate cancer.

Prostate cancer is the most common malignancy in males and the second leading cause of death from cancer in men. The majority of these patients will undergo definitive treatment. However, about 35% are expected to have biochemical recurrence within 10 years. Currently, no commercially available molecular imaging agent can effectively localize regional prostate metastases in soft tissue. Talab et al., Radiol Clin North Am; 50 (6): 1015-1041 (2012). The development of a sensitive and specific method to non-invasively localize prostate cancer in its early stages within the prostate and in local pelvic lymph nodes would profoundly change the workup and management of prostate cancer.

Small molecule inhibitors of prostate specific membrane antigen (PSMA) have shown the potential to be good agents for prostate cancer imaging. PSMA is a type II membrane protein with a very short intracellular domain connected by a single transmembrane helix to a large extracellular domain. Israeli et al., Cancer Res; 53 (2): 227-230 (1993). PSMA was first identified as the molecular target of the 7E11-C5 antibody which selectively binds LNCaP cells. In addition to its normal expression in the central nervous system, urogenital system, and small bowel, PSMA is overexpressed on prostate cancer cells and tumor neovasculature. A simple, easy to synthesize, and yet potent, urea-based small molecule inhibitor of PSMA was first published in 2001. Kozikowski et al., J Med Chem; 44 (3): 298-301 (2001). During the last decade, the simple di-amino acid urea compounds first made by Kozikowski et al. have evolved into a myriad of imaging agents for single photon emission tomography (SPECT) and positron emission tomography (PET).

Small molecule PET and SPECT PSMA tracers that have been tested in animals and humans have demonstrated a great advancement compared to antibody-based SPECT imaging with $^{111}$In-capromab pendetide. $^{18}$F-DCFBC was the first PSMA-targeting PET tracer to be tested in humans. Cho et al., J Nucl Med; 53(12):1883-1891 (2013). In a small five-patient trial, $^{18}$F-DCFBC detected lymph node and bone metastases at 2 hr post injection. In a seven-patient phase 1 study of $^{123}$I-MIP-1072 and $^{123}$I-MIP-1095, the SPECT tracer also demonstrated detection of soft tissue and bone metastases, as well as tumors in the prostate bed. Barrett et al., J Nucl Med; 54 (3): 380-387 (2013). Afshar-Oromieh et al. tested Glu-NH—CO—NHLys(Ahx)-[$^{68}$Ga(HBED-CC)] in 37 patients with prostate cancer and demonstrated a (per patient) lesion detection rate of 60% at PSA $<$2.2 ng/ml and a detection rate of 100% at PSA $>$2.2 ng/ml. Afshar-Oromieh et al., Eur J Nucl Med Mol Imaging; 40 (4): 486-495 (2013). All of these early human trials showed good lesion to background contrast at a few hours post injection compared to $^{111}$In-capromab penditide images, which need to be acquired 4 days post injection. However, $^{18}$F-DCFBC also had elevated liver background and unexpected blood pool retention. $^{123}$I-MIP-1072, $^{123}$I-MIP-1095, and Glu-NH—CO—NH-Lys (Ahx)-[$^{68}$Ga(HBEDCC) all showed significant uptake in salivary glands, lacrimal glands, and liver. These organs have no significant expression of PSMA. When the tracer molecules are used as diagnostic agents, the elevated background affects the overall sensitivity of detection. If these agents would be used for therapy, unintended background would increase the overall toxicity of the treatment.

The non-PSMA related background activity exhibited by the current tracers may be due to hydrophobic interactions. Small radiolabeled PSMA tracers contain an aromatic group for convenient radiohalogenation. Many of the imaging agents with bulky NIR fluorophores and radionuclide chelates have long slender hydrophobic linkers that join the fluorophore or metal chelate to the di-amino acid urea moiety. A long linker is necessary because a 20 Å substrate tunnel connects the surface of PSMA with its deep ectodomain. Mesters et al., EMBO J.; 25 (6): 1375-1384 (2006). Early design efforts with $^{99m}$Tc tracers demonstrated that there is a minimal linker length needed for proper binding. Banerjee et al., J. Med Chem; 51 (15): 4504-4517 (2008). In the available high-resolution structures (such as PDB 3D7G and 3D7H), where space allows, only a few crystallographic water molecules are seen within the tunnel. Given the known structure of PSMA, one would expect low binding affinity for RBI-1033, a urea-based PSMA targeting compound containing a bulky 2-5 Å moiety in the substrate tunnel region. Cramer Nucleosides Nucleotides Nucleic Acids; 26

(10-12): 1471-1477 (2007). The axial dimension of the 2-5 Å moiety greatly exceeds the width of the tunnel.

Surprisingly, RBI-1033 exhibits ten times higher affinity toward PSMA than its "parent" urea ligand. The high affinity of RBI-1033 and its derivatives to PSMA suggest that a bulky linker is acceptable in the substrate tunnel. Wang et al., Nucleosides Nucleotides Nucleic Acids; 31 (5): 432-444 (2012). However, there remains a need for additional compounds useful as PSMA imaging agents.

In addition to improved imaging agents, there is a need for improved therapeutic agents for treating prostate and other PSMA-expressing tumors. Earlier generations of the compounds of the disclosure provide for non-specific uptake, such as to the salivary gland or excretion through the urinary tract, that limits their usefulness for administration at therapeutic doses, which are often higher than doses used for imaging.

SUMMARY OF THE DISCLOSURE

A series of PSMA inhibitors have been designed with highly negatively charged linkers.

II

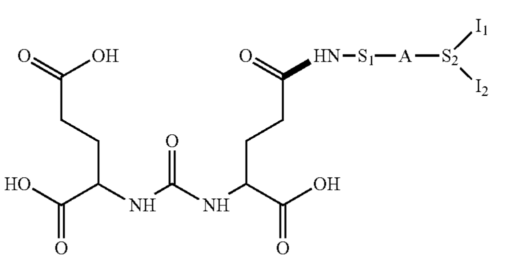

In one aspect, the present disclosure is directed to a PSMA-specific agent or a pharmaceutically acceptable salt thereof. The agent comprises a compound according to Formula II:

wherein $S_1$ is an organic spacer group comprising 3-7 carbons; A is an amino acid chain comprising 2-5 amino acids and wherein at least two amino acids are Glu; $S_2$ is optionally an organic spacer comprising 1-8 carbons; and $I_1$ comprises DOTA.

In one example of the disclosure, $S_1$ comprising 5 carbons.

In another example of the disclosure, A comprises 5 amino acids.

In another example of the disclosure, A comprises Glu-Glu-Glu.

In yet another example of the disclosure, A comprises Glu-Glu-Glu-Tyr.

In yet another example, A comprises a Lys.

In another example, A comprises a thiolysine.

In yet another example of the disclosure, A consists of Glu-Glu-Glu-Tyr-Lys.

In yet another example of the disclosure, A consists of Glu-Glu-Glu-Tyr-thioLys.

In still another example of the disclosure, $I_2$ is absent.

In another example of the disclosure, $S_2$ is absent.

In another example of the disclosure, the PSMA-specific agent has the following Formula:

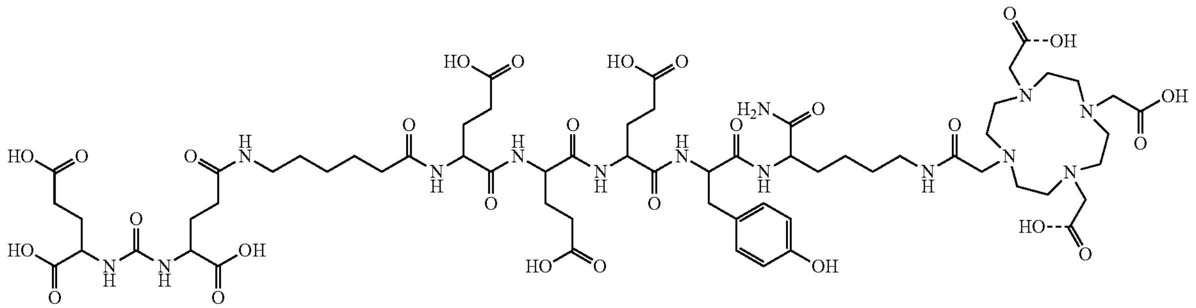

In another example of the disclosure, the PSMA-specific agent has the following Formula:

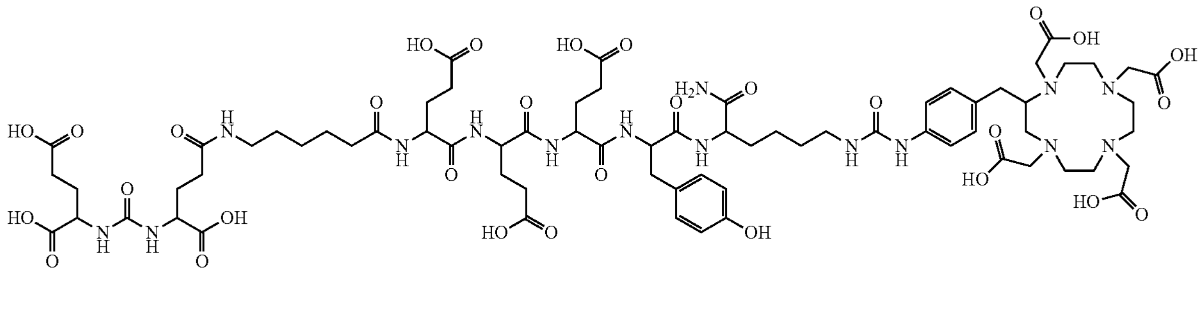 [SMILES: NC(=O)C(CCCCNC(=O)Nc1ccc(CC2CN(CC(=O)O)CCN(CC(=O)O)CCN(CC(=O)O)CCN2CC(=O)O)cc1)NC(=O)C(Cc1ccc(O)cc1)NC(=O)C(CCC(=O)O)NC(=O)C(CCC(=O)O)NC(=O)C(CCC(=O)O)NC(=O)CCCCCNC(=O)CCC(NC(=O)NC(CCC(=O)O)C(=O)O)C(=O)O]

In a further example of the disclosure, the PSMA-specific is radiolabeled at $I_1$ and/or $I_2$.

In second aspect of the disclosure is a method of imaging a cancer cell. The method comprises administering to a patient a PSMA-specific agent according to the disclosure and monitoring an output from the agent.

In an example of the second aspect, the PSMA-specific agent further comprises a radionuclide suitable for PET or SPECT imaging.

In another example of the second aspect, the radionuclide is selected from the group consisting of a radioactive isotope of Cu, Tc, F, Ga, Lu, Y, Sm, Lu, At, Tb, Zr, Sc, and Ac.

In another example of the second aspect, the imaging is PET imaging.

In a third aspect of the disclosure is a method of treating a cancer. The method comprising administering to a patient in need thereof a PSMA-specific agent according to the disclosure.

In an example of the second and third aspects, the PSMA-specific agent used for imaging is the same as the PSMA-specific agent used for treatment.

DETAILED DESCRIPTION OF THE DISCLOSURE

Figure 1:
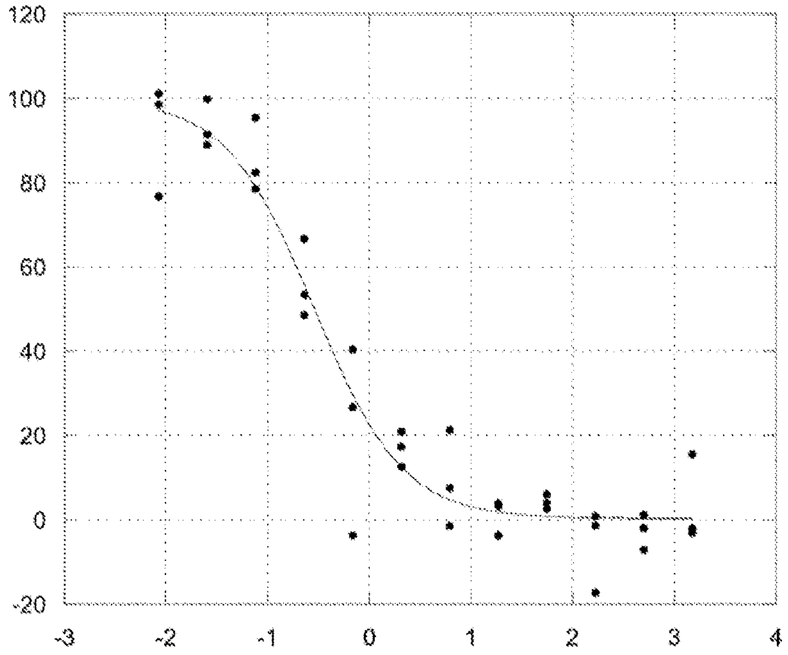
FIG. 1 provides the results of a competitive binding assay for Compound 1 in PC3-PIP PSMA-expressing cells (x-axis: concentration of Compound 1 (log (nm); y-axis: normalized fluorescence).

Through iterative re-design of RBI-1033, it has been found that the linker region is amenable to further engineering and one can construct PSMA tracers with negatively charged linker regions.

Example embodiments will now be described more fully hereinafter with reference to the accompanying figures in which example embodiments and representative data are shown. Whenever possible, the same reference numerals are used throughout the drawings to refer to the same or like parts. However, the embodiments may take on many different forms and should not be construed as limited to those specifically set forth herein. These example embodiments are provided so that this disclosure will be both thorough and complete, and will fully convey the scope of the claims to those skilled in the art.

The terminology as set forth herein is for description of the disclosure only and should not be construed as limiting of the disclosure as a whole. Unless otherwise specified, "a," "an," "the," and "at least one" are used interchangeably. Furthermore, as used in the description of the disclosure and the appended claims, the singular forms "a", "an", and "the" are inclusive of their plural forms, unless contraindicated by the context surrounding such. As used herein, the term "about" means that amounts, sizes, Formulations, parameters, and other quantities and characteristics are not and need not be exact, but may be approximate and/or larger or smaller, as desired, reflecting tolerances, conversion factors, rounding off, measurement error and the like, and other factors known to those of skill in the art, as such variations are appropriate to perform the disclosed methods. When the term "about" is used in describing a value or an endpoint of a range, the disclosure should be understood to include the specific value or endpoint referred to. Whether or not a numerical value or endpoint of a range in the specification recites "about," the numerical value or endpoint of a range is intended to include two embodiments: one modified by "about," and one not modified by "about." It will be further understood that the endpoints of each of the ranges are significant both in relation to the other endpoint, and independently of the other endpoint.

Definitions

Unless defined otherwise, all technical and scientific terms used herein have the same meaning as commonly understood by one of ordinary skill in the art to which the disclosure pertains. Although any methods and materials similar or equivalent to those described herein can be used in the practice for testing of the present disclosure, the preferred materials and methods are described herein. In describing and claiming the present disclosure, the following terminology will be used.

"Image" or "imaging" refers to a procedure that produces a picture of an area of the body, for example, organs, bones, tissues, or blood.

As used herein, "therapy" refers to any procedure that treats a disease state. In particular, "radiotherapy" refers to a procedure that utilizes high energy ionizing radiation to kill cancer cells and/or shrink tumors.

"Pharmaceutically acceptable" as used herein means that the compound or composition is suitable for administration to a subject for the methods described herein, without unduly deleterious side effects.

As used herein, "a detectably effective amount" of the agent of the disclosure is defined as an amount sufficient to yield an acceptable image using equipment which is available for clinical use. A detectably effective amount of an imaging agent of the disclosure may be administered in more than one injection. The detectably effective amount of the imaging agent of the disclosure can vary according to factors such as the degree of susceptibility of the individual, the age, sex, and weight of the individual, idiosyncratic responses of the individual, and the dosimetry. Detectably effective amounts of the imaging agent of the disclosure can also vary according to instrument and film-related factors. Optimization of such factors is well within the level of skill in the art. The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

As used herein, "a therapeutically effective amount" of the agent of the disclosure is defined as an amount sufficient to elicit the killing of cancer cells. A therapeutically effective amount of the agent of the disclosure may be administered in more than one injection. The therapeutically effective amount of the imaging agent of the disclosure can vary according to factors such as the degree of susceptibility of the individual, the age, sex, and weight of the individual, idiosyncratic responses of the individual, and the dosimetry. Optimization of such factors is well within the level of skill in the art. The amount of agent used for therapeutic purposes and the duration of the treatment will depend upon the radionuclide used to label the agent, the body mass of the patient, the nature and severity of the condition being treated, the nature of therapeutic treatments which the patient has undergone or is concurrently undergoing, and on the idiosyncratic responses of the patient. Ultimately, the attending physician will decide the amount of agent to administer to each individual patient and the duration of the therapy.

The terms "comprising" and variations thereof do not have a limiting meaning where these terms appear in the description and claims.

As used herein, the term "organic group" is used for the purpose of this disclosure to mean a hydrocarbon group that is classified as an aliphatic group, cyclic group, or combination of aliphatic and cyclic groups (e.g., alkaryl and aralkyl groups). In the context of the present disclosure, suitable organic groups for PSMA-specific agents are those that do not interfere with the compounds' activity. In the context of the present disclosure, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some instances, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

Cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms "O", "S" or 'N".

When a group is present more than once in any Formula or scheme described herein, each group (or substituent) is independently selected, whether explicitly stated or not. For example, for the Formula —C(O)—$NR_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The term "amino acid" as used herein is understood to mean an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Natural amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Other amino acids include, but not limited to, arginosuccinic acid, citrulline, cysteine sulfinic acid, 3,4-dihydroxyphenylalanine, homocysteine, homoserine, ornithine, carnitine, selenocysteine, selenomethionine, 3-monoiodotyrosine, 3,5-diiodotryosine, 3,5,5'-triiodothyronine, and 3,3',5,5'-tetraiodothyronine.

Compounds described herein can exist or be converted to a pharmaceutically acceptable salt. The salts can be prepared by treating the free acid with an appropriate amount of a chemically or pharmaceutically acceptable base. Representative chemically or pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In particular, pharmaceutically acceptable salts can include any salt that is or can be approved for use as a pharmaceutical agent. In one aspect, the reaction is conducted in water, alone or in combination with an inert, water-miscible organic solvent, at a temperature of from about 0° C. to about 100° C. (e.g. at room temperature). The molar ratio of the compound to base used is chosen to provide the ratio desired for particular salts. For preparing, for example, the ammonium salts of the free acid starting material, the starting material can be treated with approximately one equivalent of base to yield a salt.

Certain compounds described herein may exist in particular geometric or stereoisomeric forms. The present disclosure contemplates all such compounds, including cis- and trans-isomers, R- and S-enantiomers, diastereomers, (1))-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure.

Prostate specific membrane antigen (PSMA) is a type II membrane protein with a very short intracellular domain connected by a single transmembrane helix to a large extracellular domain. PSMA is overexpressed on most solid tumor neovasculature, as well as in prostate cancer, and is therefore a useful target for imaging agents. Chang et al., Cancer Res. 59, 3192-3198 (1999). For further information regarding the prostate specific membrane antigen, see US Patent Publication No. 2007/0148662, the disclosure of which is incorporated herein by reference.

PSMA-Specific Agents

PSMA-specific, as used herein, refers to the fact that imaging and therapeutic agents bind to prostate specific membrane antigen (PSMA) specifically or preferentially relative to other biomaterial. As used herein, the term "specifically binding" refers to the interaction of the agent with a second chemical species, wherein the interaction is dependent upon the presence of a particular structure (e.g., an antigenic determinant or epitope) on the chemical species; for example, the imaging agent recognizes and preferentially or specifically binds to a specific protein structure of PSMA rather than to proteins generally.

One aspect of the present disclosure includes a PSMA-specific imaging or therapeutic agent or a pharmaceutically acceptable salt thereof comprising a compound according to Formula I or Formula II:

I

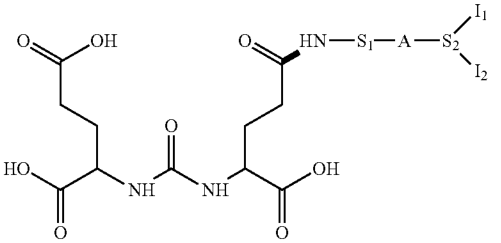

II

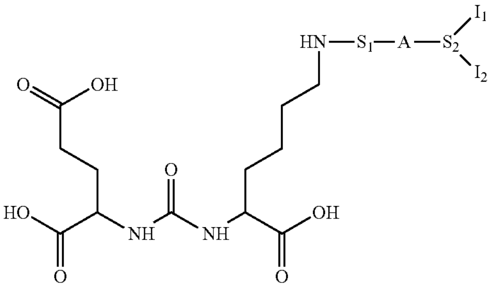

The PSMA-specific agents of Formula I and Formula II include three main regions: a PSMA binding region, a linker region including the organic spacer groups $S_1$ and $S_2$ as well as a negatively charged amino acid chain A, and the imaging group region which can be used for both imaging and therapy.

The PSMA binding region includes a urea ligand based on either Glu(O)Glu or Glu(O)Lys. The PSMA binding region is covalently connected to the linker region. In one preferred aspect, the PSMA binding region are covalently linked through a bond between two amino acids. The covalent linkage can be a peptide bond, a peptoid bond, or a bond between the backbone of one amino acid and the side chain of another.

The linker region serves to separate the imaging group and the PSMA binding region. The negatively charged amino acid chain A is negatively charged as a result of including one or more negatively charged amino acids. Examples of negatively charged amino acids include glutamic acid and aspartic acid. In certain aspects D-glutamic acid can be used. In some aspects one, two, or three of the amino acids are negatively charged. In some examples the one or more negatively charged amino acids is glutamic acid. The amino acids are linked through peptide bonds (linked through either the main chain or the side chain) to form a relatively short negatively charged peptide oligomer having a length of 1 to 5 amino acids. In one aspect the negatively charged amino acid chain A is Glu. In another aspect the negatively charged amino acid chain A is Glu-Glu. In a further example the negatively charged amino acid chain A is Glu-Glu-Glu.

Adjacent to the negatively charged amino acid chain A are two organic spacer groups, designated $S_1$ and $S_2$ in Formula I. The organic spacer groups $S_1$ and $S_2$ connect the negatively charged amino acid chain A to the PSMA binding region and the imaging group, respectively.

In certain aspects $S_1$ is absent or is an organic spacer group comprising 3-10 carbons. In some examples $S_1$ has the structure

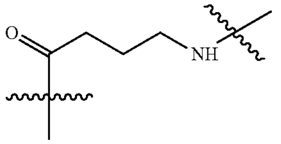

In certain aspects $S_2$ is absent or is an organic spacer group comprising 1 to 15 carbons and 0 to 2 amino acids. In some examples, $S_2$ is selected from

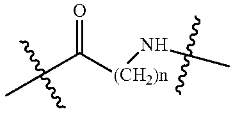

,

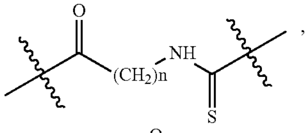

, and

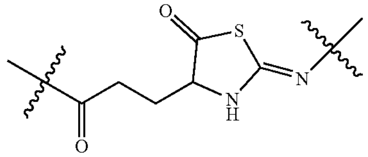

where n is from 3 to 5.

In other examples, $S_2$ is

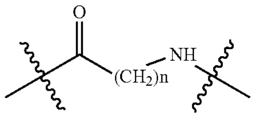

and one amino acid where n is from 3 to 5.

In further examples, $S_2$ is

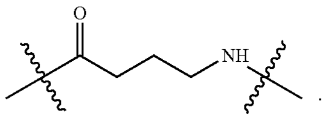 [SMILES: *NCCCC(*)=O]

In even further examples, $S_2$ is

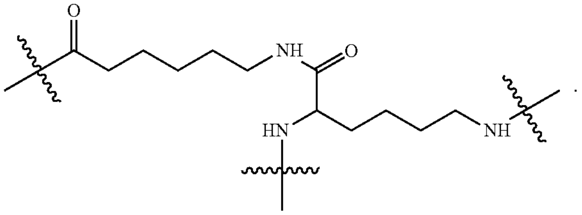 [SMILES: *NCCCCC(N*)C(=O)NCCCCCC(*)=O]

In still further examples, $S_2$ is an organic spacer comprising 1-8 carbons. In one embodiment, $S_2$ comprises an aryl group, specifically a phenyl group. In another embodiment, $S_2$ is absent from the agent.

The PSMA-specific agent also includes an imaging group used for imaging and/or therapy. In the case of imaging, the imaging group is a structure that allows the agent to be detected using an appropriate imaging device. In the case of therapy, the imaging group is a structure that allows the delivery of a toxin, e.g., a radionuclide, to the targeted site. Examples of imaging groups include near infrared imaging agents, positron emission tomography imaging agents, single-photon emission tomography agents, fluorescent compounds, radioactive isotopes, and MRI contrast agents. The detectable imaging group can be any material having a detectable physical or chemical property. Such imaging groups have been well-developed and, in general, most any imaging group can be used in the present disclosure. Thus, an imaging group is any composition detectable by spectroscopic, photochemical, biochemical, immunochemical, electrical, optical or chemical means. The choice of imaging group depends on sensitivity required, ease of conjugation with the compound, stability requirements, available instrumentation, and disposal provisions. A comprehensive review of imaging agents and their imaging groups can be found in the Molecular Imaging and Contrast Agents Database (MICAD), developed by the National Center for Biotechnology Information, which is incorporated herein by reference.

In one aspect, the present disclosure includes imaging groups having the following structures:

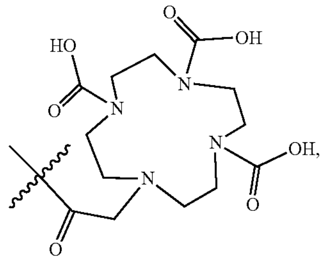

-continued

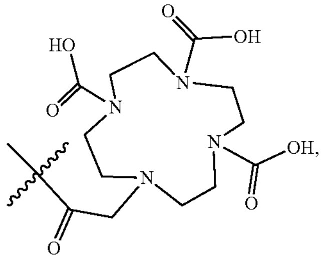

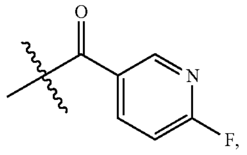

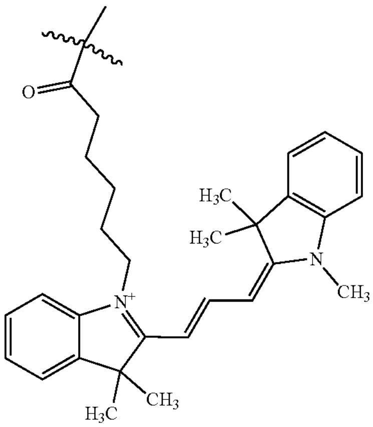

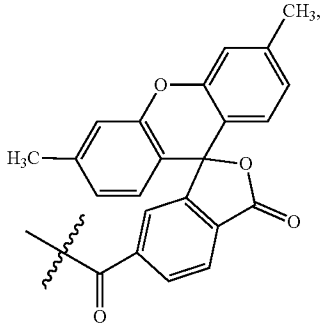

and

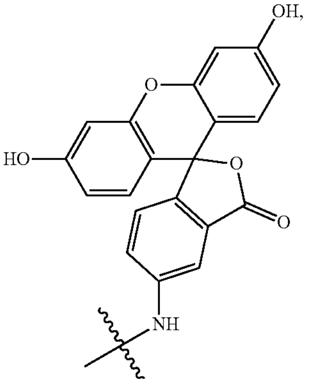

-continued

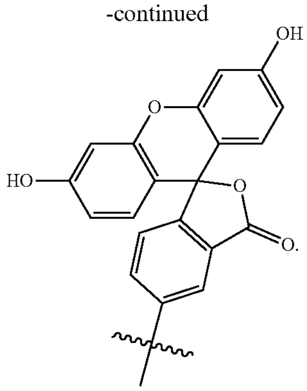

In some instances, the imaging group comprises a radioisotope. Specific exemplary radioisotopes include $^{18}$F, $^{64}$Cu, $^{90}$Y, $^{99m}$Tc $^{123}$I, $^{124}$I, $^{125}$I, $^{126}$I, $^{131}$I, $^{75}$Br, $^{76}$Br, $^{77}$Br, $^{80}$Br, $^{80m}$Br, $^{82}$Br, $^{83}$Br, $^{44}$Sc, $^{68}$Ga, $^{89}$Zr, $^{153}$Sm, $^{177}$Lu, $^{225}$Ac and $^{211}$At. Radioisotope-containing compounds of the present disclosure can be prepared with sufficient radiolabel to be used in imaging and/or therapeutic applications. In other words, the compounds can be prepared with radioisotope concentrations greater than natural abundance, when a particular radioisotope occurs naturally.

Radiolabeled compounds may be used for diagnostic, imaging, or therapeutic purposes. For example, some compounds, e.g. those labeled with $^{125}$I and $^{123}$I, are designed for SPECT imaging, while some compounds, e.g. those labeled with $^{18}$F, $^{68}$Ga, $^{64}$Cu and $^{124}$I, are designed for PET imaging, and some radioisotopically labeled compounds, e.g. those labeled with $^{67}$Cu, $^{64}$Cu, $^{177}$Lu, $^{90}$Y, $^{153}$Sm, $^{225}$Ac and $^{211}$At may be used therapeutically. In general, the suitability of a particular radioisotope for a particular purpose is well understood in the art.

In some instances, the present disclosure includes the following labeled imaging groups in Table 1:

TABLE 1

| Imaging Group | Exemplary Labels |
|---|---|
| 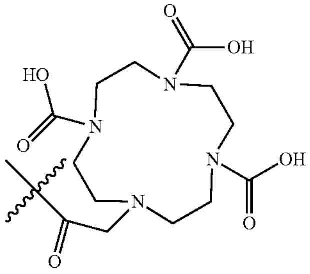 [SMILES: *C(=O)CN1CCN(C(=O)O)CCN(C(=O)O)CCN(C(=O)O)CC1] | For imaging: $^{68}$Ga, $^{89}$Zr, $^{62}$Cu, $^{64}$Cu, $^{99m}$Tc For therapy: $^{90}$Y, $^{67}$Cu, $^{64}$Cu, $^{177}$Lu, $^{225}$Ac, Bi, $^{99m}$Tc |

TABLE 1-continued

| Imaging Group | Exemplary Labels |
|---|---|
| 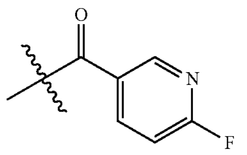 [SMILES: *C(=O)c1ccc(F)nc1] | For imaging: $^{18}$F |

Various fluorochromes are commercially available and can be used as near infrared imaging groups for the imaging agents of the disclosure. Exemplary fluorochromes include, for example, Cy5.5, Cy5 and Cy7 (GE Healthcare); AlexaFlour660, AlexaFlour680, AlexaFluor750, and AlexaFluor790 (Invitrogen); VivoTag680, VivoTag-5680, and VivoTag-S750 (PerkinElmer); Dy677, Dy682, Dy752 and Dy780 (Dyomics); DyLight488, DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source) and Kodak X-SIGHT 650, Kodak X-SIGHT 691, Kodak X-SIGHT 751 (Carestream Health). An example of a PSMA-specific agent including a near-infrared imaging group is ZJ-MCC-dEdEdEGK(IRDye800cw)G.

In some aspects, the imaging group is suitable for use as a magnetic resonance imaging agent. Disease detection using MRI is often difficult because areas of disease have similar signal intensity compared to surrounding healthy tissue. In the case of magnetic resonance imaging, the imaging agent can also be referred to as a contrast agent. Lanthanide elements are known to be useful as contrast agents. The lanthanide chemical elements comprises the fifteen metallic chemical elements with atomic numbers 57 through 71, and include lanthanum, cerium, praseodymium, neodymium, promethium, samarium, europium, gadolinium, terbium, dysprosium, holmium, erbium, thulium, ytterbium, and lutetium. In some examples the lanthanides used include europium, gadolinium, and terbium. In order to more readily handle these rare earth metals, the lanthanides can be chelated. In some instances, the lanthanide selected for use as an imaging group is gadolinium, or more specifically gadolinium (III).

In some embodiments, the PSMA-specific agent includes two imaging groups, $I_1$ and $I_2$. In some embodiments, the PSMA-specific agent includes one imaging group, such that $I_2$ is absent from the compound.

Another aspect of the present disclosure can include the following PSMA-specific agents in Table 2:

TABLE 2
| Compound Number | Structure |
| --- | --- |
| 1 | 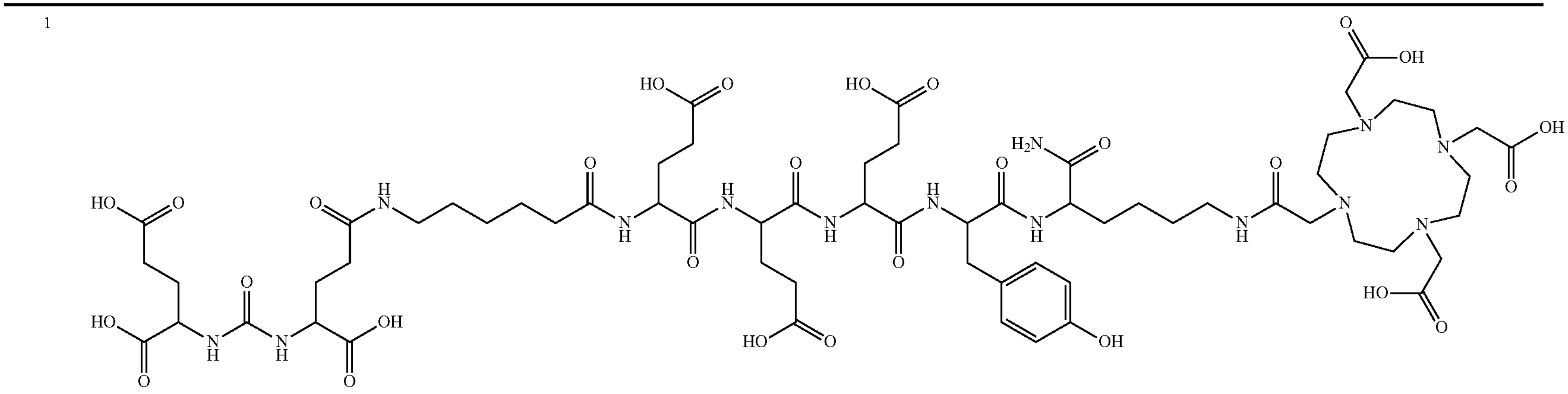 |
| 2 | 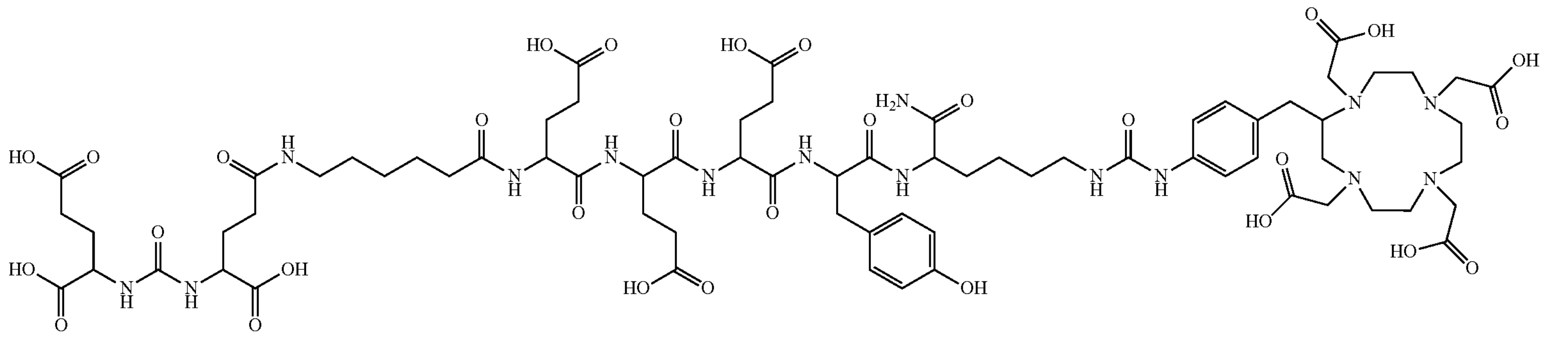 [SMILES: NC(=O)C(CCCCNC(=O)Nc1ccc(CC2CN(CC(=O)O)CCN(CC(=O)O)CCN(CC(=O)O)CCN2CC(=O)O)cc1)NC(=O)C(Cc1ccc(O)cc1)NC(=O)C(CCC(=O)O)NC(=O)C(CCC(=O)O)NC(=O)C(CCC(=O)O)NC(=O)CCCCCNC(=O)CCC(NC(=O)NC(CCC(=O)O)C(=O)O)C(=O)O] |

TABLE 2-continued
| Compound Number | Structure |
| --- | --- |
| 3 | 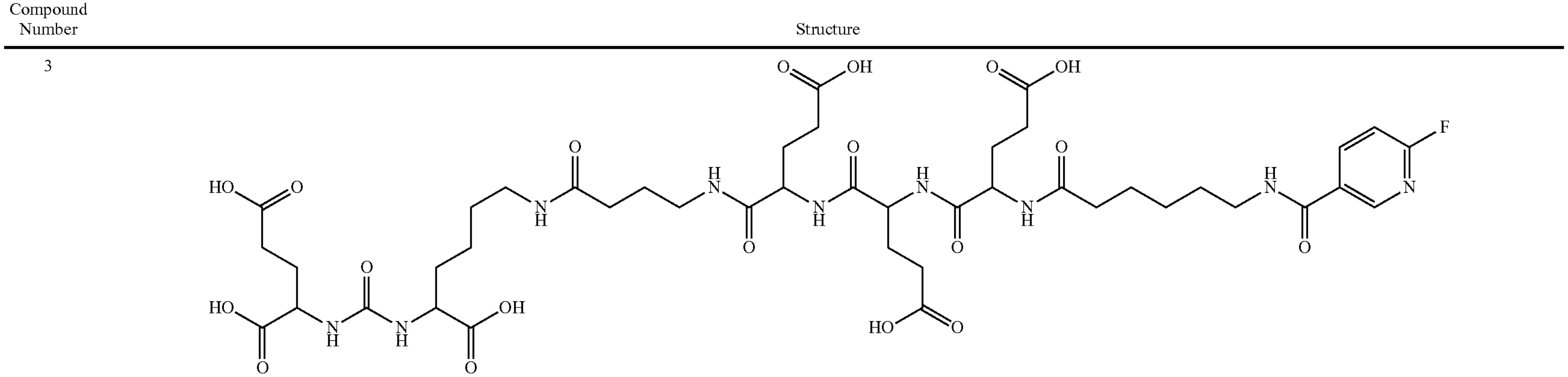 |
| 4 | 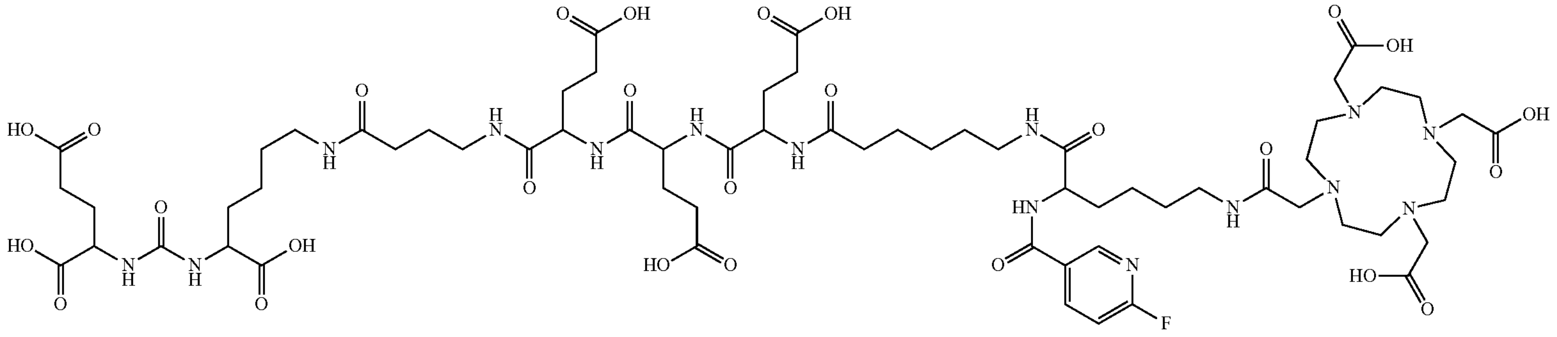 [SMILES: O=C(O)CCC(NC(=O)NC(CCCCNC(=O)CCCNC(=O)C(CCC(=O)O)NC(=O)C(CCC(=O)O)NC(=O)C(CCC(=O)O)NC(=O)CCCCCNC(=O)C(CCCCNC(=O)CN1CCN(CC(=O)O)CCN(CC(=O)O)CCN(CC(=O)O)CC1)NC(=O)c1ccc(F)nc1)C(=O)O)C(=O)O] |

TABLE 2-continued
| Compound Number | Structure |
|---|---|
| 5 | 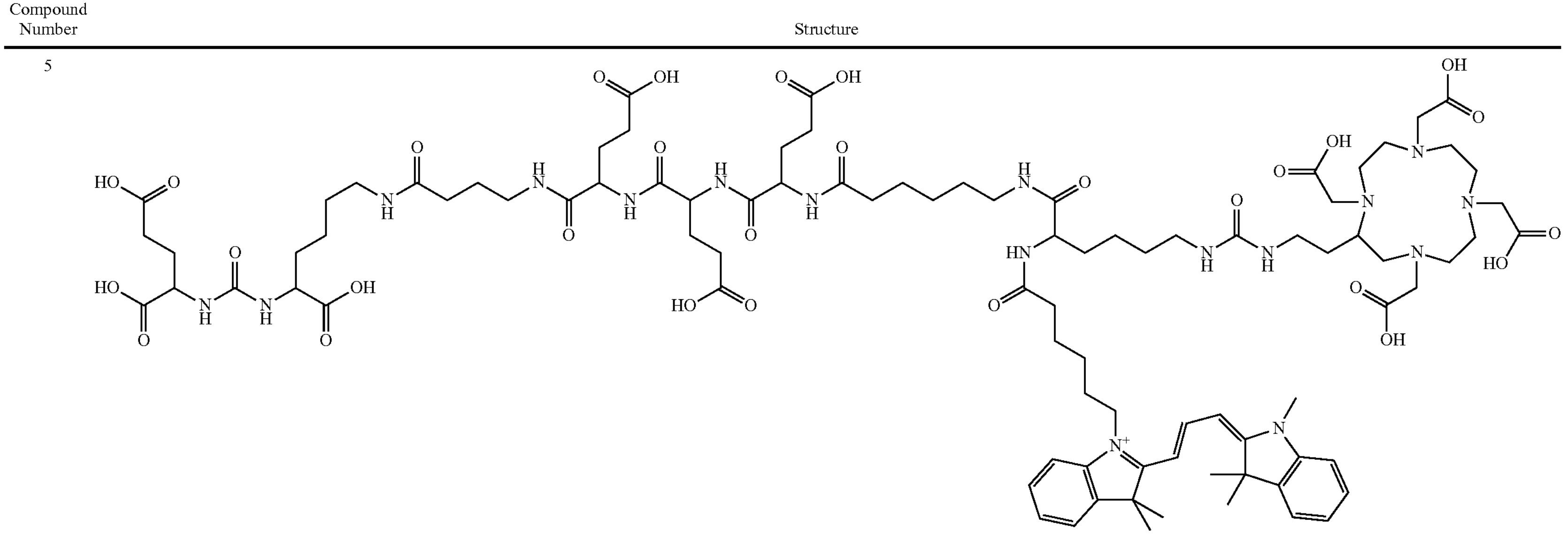 |
| 6 | 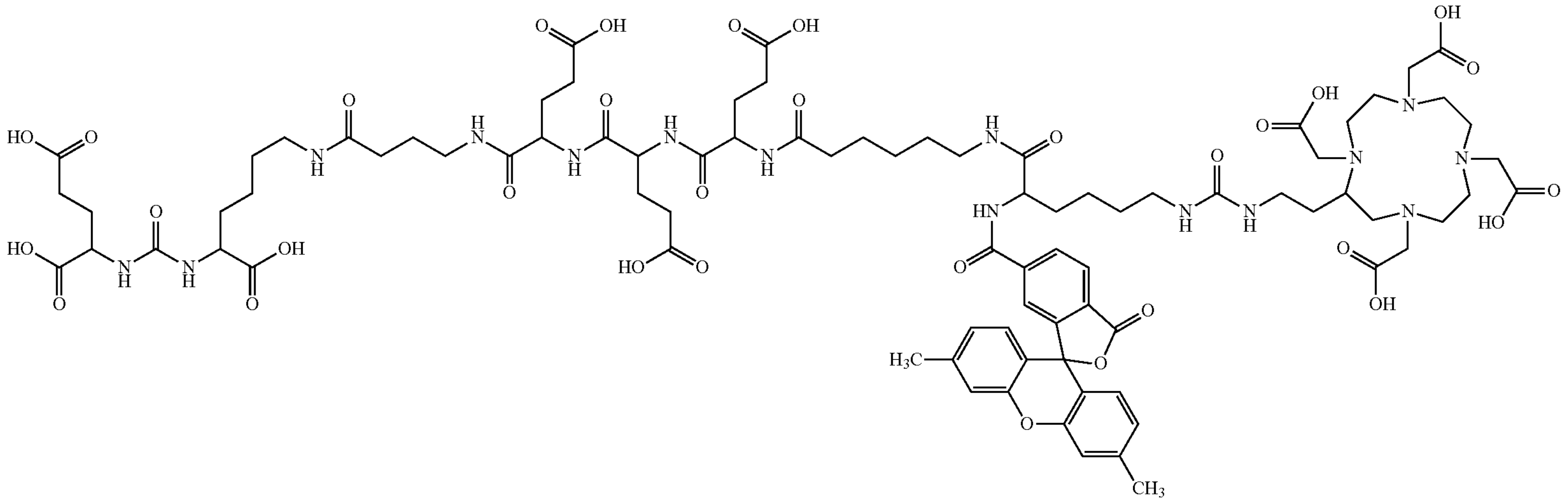 [SMILES: Cc1ccc2c(c1)Oc1cc(C)ccc1C21OC(=O)c2ccc(C(=O)NC(CCCCNC(=O)NCCC3CN(CC(=O)O)CCN(CC(=O)O)CCN(CC(=O)O)CCN3CC(=O)O)C(=O)NCCCCCC(=O)NC(CCC(=O)O)C(=O)NC(CCC(=O)O)C(=O)NC(CCC(=O)O)C(=O)NCCCC(=O)NCCCCC(NC(=O)NC(CCC(=O)O)C(=O)O)C(=O)O)cc21] |

TABLE 2-continued
| Compound Number | Structure |
| --- | --- |
| 7 | 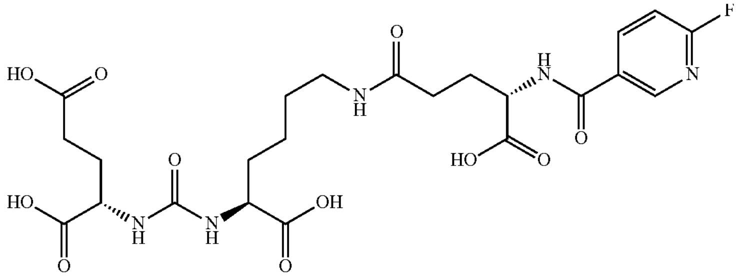 [SMILES: O=C(O)CC[C@H](NC(=O)N[C@@H](CCCCNC(=O)CC[C@H](NC(=O)c1ccc(F)nc1)C(=O)O)C(=O)O)C(=O)O] |
| 8 | 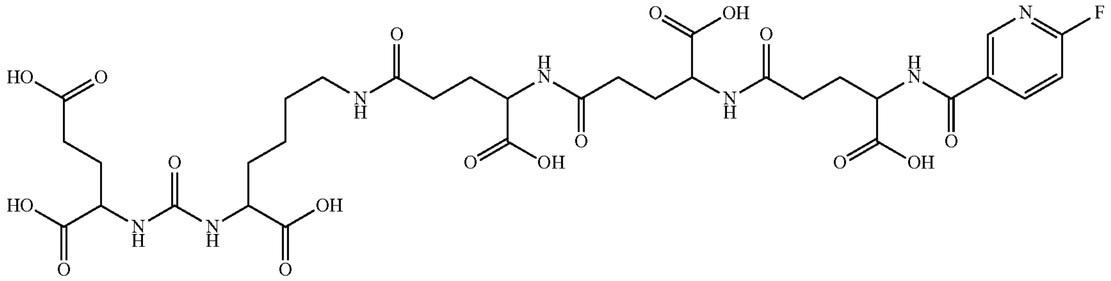 [SMILES: O=C(O)CCC(NC(=O)NC(CCCCNC(=O)CCC(NC(=O)CCC(NC(=O)CCC(NC(=O)c1ccc(F)nc1)C(=O)O)C(=O)O)C(=O)O)C(=O)O)C(=O)O] |
| 9 | 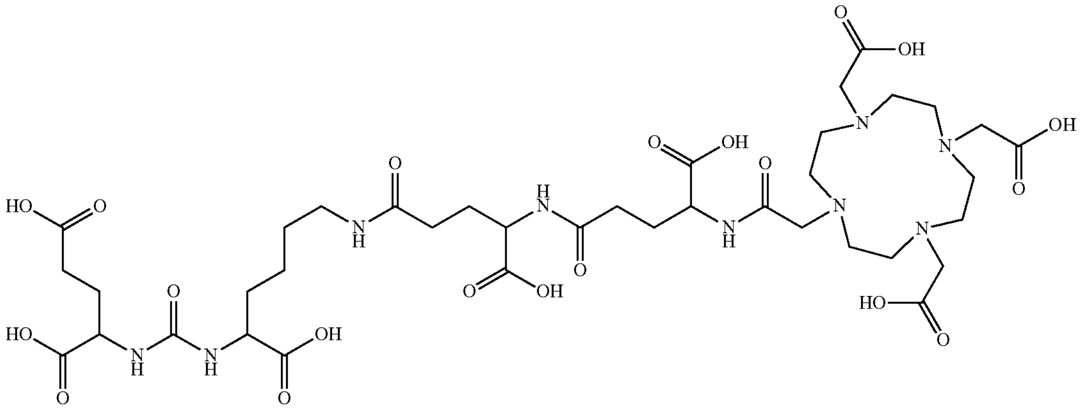 [SMILES: O=C(O)CCC(NC(=O)NC(CCCCNC(=O)CCC(NC(=O)CCC(NC(=O)CN1CCN(CC(=O)O)CCN(CC(=O)O)CCN(CC(=O)O)CC1)C(=O)O)C(=O)O)C(=O)O)C(=O)O] |

TABLE 2-continued
| Compound Number | Structure |
| --- | --- |
| 10 | 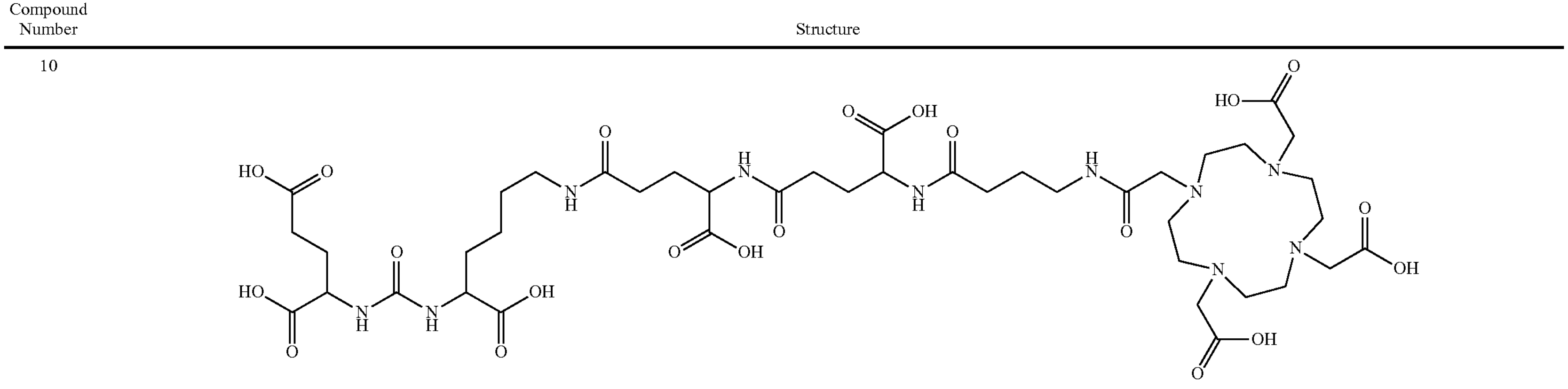 |
| 11 | 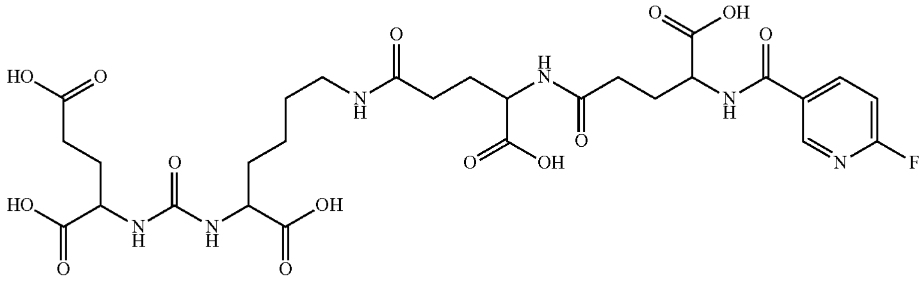 [SMILES: O=C(O)CCC(NC(=O)NC(CCCCNC(=O)CCC(NC(=O)CCC(NC(=O)c1ccc(F)nc1)C(=O)O)C(=O)O)C(=O)O)C(=O)O] |
| 12 | 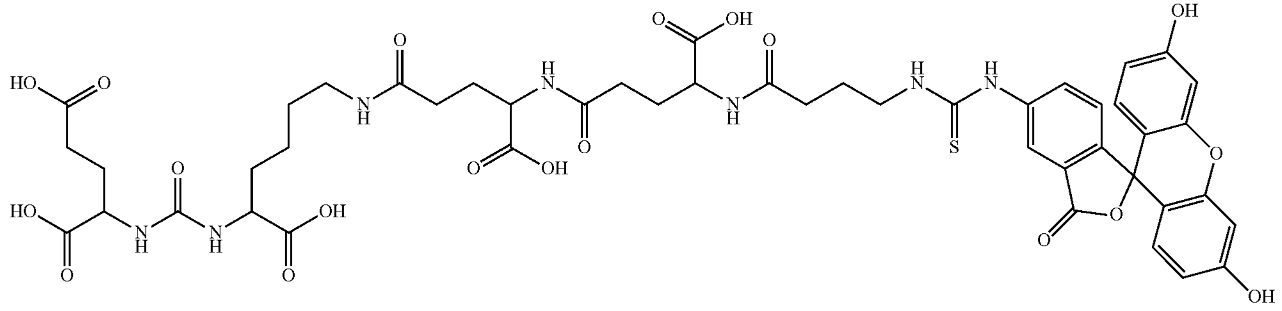 [SMILES: O=C(O)CCC(NC(=O)NC(CCCCNC(=O)CCC(NC(=O)CCC(NC(=O)CCCNC(=S)Nc1ccc2c(c1)C(=O)OC21c2ccc(O)cc2Oc2cc(O)ccc21)C(=O)O)C(=O)O)C(=O)O)C(=O)O] |

TABLE 2-continued
| Compound Number | Structure |
| --- | --- |
| 13 | 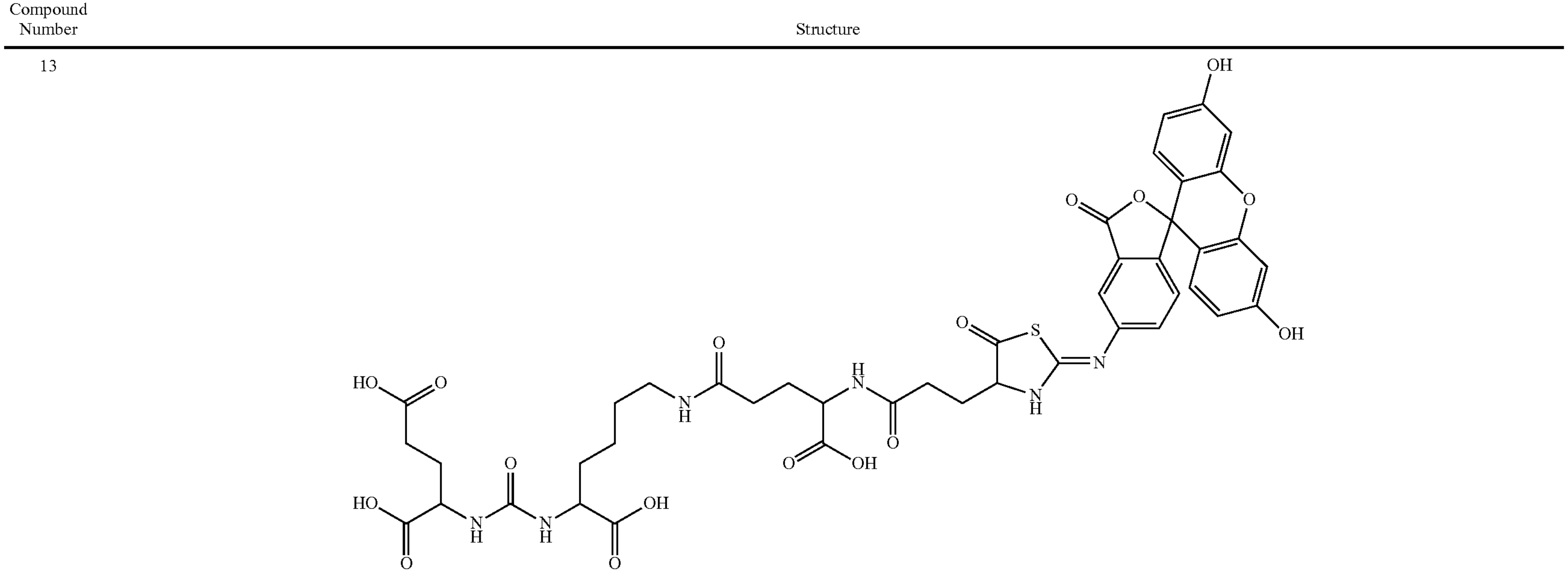 |
| 14 | 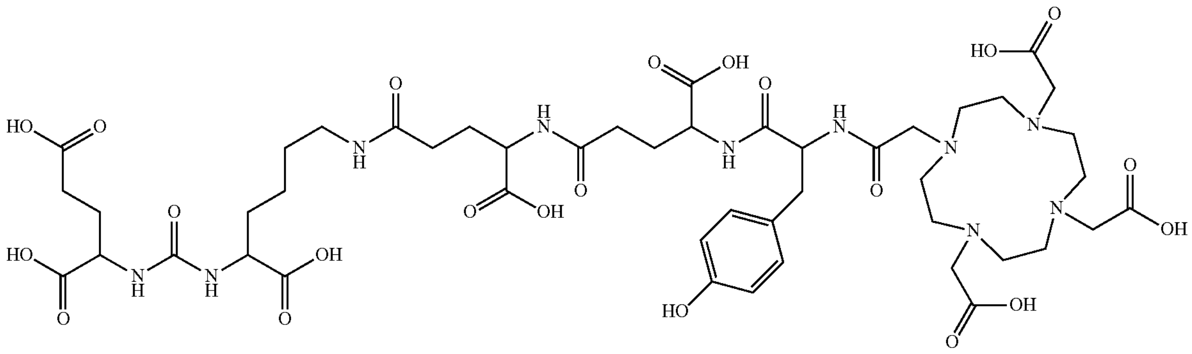 [SMILES: O=C(O)CCC(NC(=O)NC(CCCCNC(=O)CCC(NC(=O)CCC(NC(=O)C(Cc1ccc(O)cc1)NC(=O)CN1CCN(CC(=O)O)CCN(CC(=O)O)CCN(CC(=O)O)CC1)C(=O)O)C(=O)O)C(=O)O)C(=O)O] |

TABLE 2-continued
| Compound Number | Structure |
|---|---|
| 15 | 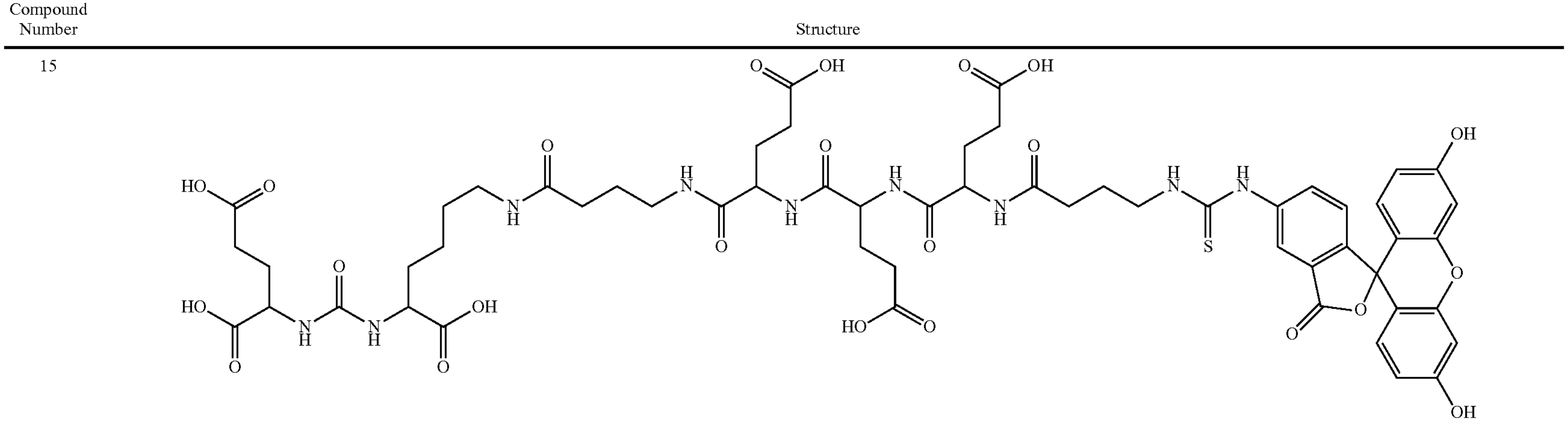 |
| 16 | 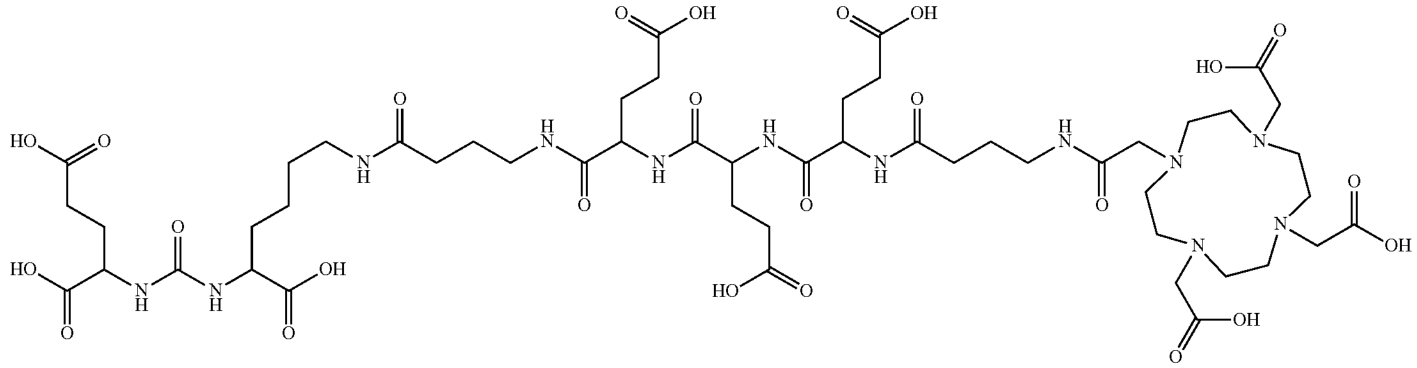 [SMILES: O=C(O)CCC(NC(=O)NC(CCCCNC(=O)CCCNC(=O)C(CCC(=O)O)NC(=O)C(CCC(=O)O)NC(=O)C(CCC(=O)O)NC(=O)CCCNC(=O)CN1CCN(CC(=O)O)CCN(CC(=O)O)CCN(CC(=O)O)CC1)C(=O)O)C(=O)O] |

Methods of Imaging a Tissue Region Using a PSMA-Specific Imaging Agent.

Another aspect of the disclosure provides a method for imaging prostate cancer in a tissue region of a subject that includes the steps of: (a) administering to the subject a detectably effective amount of a PSMA-specific imaging agent or a pharmaceutically acceptable salt thereof comprising a compound according to Formula I or Formula II:

I

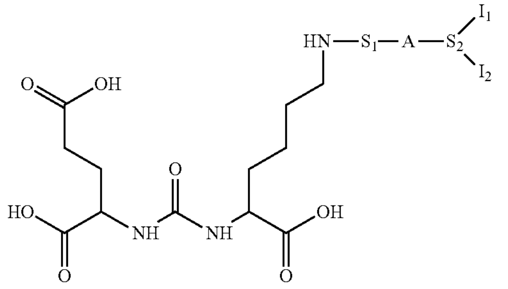

II

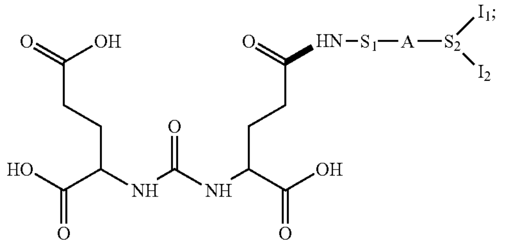

(b) allowing a sufficient amount of time for the PSMA-specific imaging agent to enter the tissue region; and (c) performing imaging of the tissue region of the subject using an imaging device capable of detecting the imaging group.

The imaging agent can be any of the imaging agents encompassed by Formula I, Formula II, and/or otherwise described herein. In some instances, the imaging device is a positron or single-photon emission tomography/computed tomography scanner, and the imaging group is a corresponding positron or single-photon emission tomography imaging group. In other aspects, the imaging device is near-infrared imaging device, and the imaging group of the imaging agent is a near-infrared imaging group.

The present disclosure provides a method of generating an image of a tissue region of a subject, by administering to the subject a detectably effective amount of a PSMA-specific imaging agent, and generating an image of the tissue region of the subject to which the imaging agent has distributed. In order to generate an image of the tissue region, it is necessary for a detectably effective amount of imaging agent to reach the tissue region of interest, but it is not necessary that the imaging agent be localized in this region alone. However, in some instances, the PSMA-specific imaging agents are targeted or administered locally such that they are present primarily in the tissue region of interest. Examples of images include two-dimensional cross-sectional views and three-dimensional images. In some aspects, a computer is used to analyze the data generated by the imaging agents in order to generate a visual image. The tissue region can be an organ of a subject such as the heart, lungs, or blood vessels. In other aspects, the tissue region can be diseased tissue, or tissue that is suspected of being diseased, such as a tumor or atherosclerotic tissue. Examples of imaging methods include optical imaging, computed tomography, positron emission tomography, single photon emission computed tomography, and magnetic resonance imaging.

Means of detecting labels in order to generate an image are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Finally, simple colorimetric labels may be detected simply by observing the color associated with the label.

In some instances, the PSMA-specific imaging agent is detected using optical imaging. Optical imaging can be fast, safe, cost effective, and highly sensitive. Scan times are on the order of seconds to minutes, there is no need for ionizing radiation, and the imaging systems can be simple to use. In addition, optical probes can be designed as dynamic molecular imaging agents that may alter their reporting profiles in vivo to provide molecular and functional information in real time. In order to achieve maximum penetration and sensitivity in vivo, the choice for most optical imaging in biological systems is within the red and near-infrared (NIR) spectral region (600-900 nm), although other wavelengths in the visible region can be used. In the NIR wavelength range, absorption by physiologically abundant absorbers such as hemoglobin or water, as well as tissue autofluorescence, is minimized.

Optical imaging includes all methods from direct visualization without use of any device and use of devices such as various scopes, catheters and optical imaging equipment, for example computer-based hardware for tomographic presentations. The imaging agents are useful with optical imaging modalities and measurement techniques including, but not limited to: endoscopy; fluorescence endoscopy; luminescence imaging; time resolved transmittance imaging; transmittance imaging; nonlinear microscopy; confocal imaging; acousto-optical imaging; photoacoustic imaging; reflectance spectroscopy; spectroscopy;

coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

In other examples, the PSMA-specific imaging agent can be detected using computed tomography. Computed tomography (CT) refers to a diagnostic imaging tool that computes multiple x-ray cross sections to produce a cross-sectional view of the vascular system, organs, bones, and tissues. Positive emissions tomography and single photon emission computed tomography refer to a diagnostic imaging tool in which the patient receives a radioactive isotope by injection or ingestion which then computes multiple x-ray cross sections to produce a cross-sectional view of the vascular system, organs, bones, and tissues to image the radioactive tracer. These radioactive isotopes are bound to compounds or drugs that are injected into the body and enable study of the physiology of normal and abnormal tissues.

Before or during these steps, an imaging device can be positioned around or in the vicinity of a subject (for example, an animal or a human) to detect signals emitted from the subject. The emitted signals can be processed to construct an image, for example, a tomographic image. In addition, the processed signals can be displayed as images either alone or as fused (combined) images.

Another aspect of the disclosure provides a method of in vivo optical imaging, wherein the illuminating and detecting steps are performed using an endoscope, catheter, tomographic system, hand-held optical imaging system, or an intraoperative microscope. In certain instances, the method is a method of in vivo imaging, wherein the presence, absence, or level of emitted signal is indicative of a disease state. In certain instances, the method is a method of in vivo imaging, wherein the method is used to detect and/or monitor a disease. In certain aspects, the disease is cancer. Another aspect of the disclosure provides a method of in vivo imaging, wherein the signal emitted by the agent is used to construct an image. In other examples, the image is a tomographic image.

An imaging system useful in the practice of the disclosure can include three basic components: (1) an appropriate source for inducing excitation of the imaging agent, (2) a system for separating or distinguishing emissions from the imaging agent, and (3) a detection system. The detection system can be hand-held or incorporated into other useful imaging devices, such as intraoperative microscopes. Exemplary detection systems include an endoscope, catheter, tomographic system, hand-held imaging system, or an intraoperative microscope.

A particularly useful emission gathering/image forming component is an endoscope. Endoscopic devices and techniques which have been used for in vivo optical imaging of numerous tissues and organs. Other types of emission gathering components are catheter-based devices, including fiber optics devices. Such devices are particularly suitable for intravascular imaging.

Once the PSMA-specific imaging agent has been administered, a sufficient amount of time for the PSMA-specific imaging agent to enter the tissue region. The time required for contrast agents to reach a tissue region are known by those skilled in the art, and can be calculated based on available software, and vary depending on the injection site and the particular tissue region.

The methods and compositions disclosed herein can be used to help a physician or surgeon to identify and characterize areas of disease, such as dysplasia and cancer, to distinguish diseased from normal tissues, such as detecting specific regions of prostate cancer within an organ or other tissues that are difficult to detect using ordinary imaging techniques, and to further assess said tissues as candidates for particular treatment regimens, or gauge the prognosis such as staging the cancer. The methods and compositions disclosed herein can also be used in the detection, characterization and/or determination of the localization of a disease, including early disease, the severity of a disease or a disease-associated condition, the staging of a disease, and/or monitoring a disease. The presence, absence, or level of an emitted signal can be indicative of a disease state.

The PSMA-specific imaging agents disclosed herein can be used to image a wide variety of different types of tissue regions. Examples of different types of tissue regions include portions of the cardiovascular system, such as the heart, blood vessels, carotid arteries, and the aorta; lung tissue, adipose tissue, brain tissue, hepatic tissue, renal tissue, and prostate tissue. All of these tissues can readily be imaged by injection of the PSMA-specific imaging agents. Note that while PSMA-specific imaging agents are typically used to image a particular tissue region of interest, they can also be used to image an organ, or a whole body.

A prostate cancer tumor can be imaged using PSMA either at the prostate, or at other tissues subsequent to metastasis. Unlike many other cancers, prostate cancer is particularly difficult to detect using existing molecular imaging tracers. There are several reasons for this, including the relatively slow growth and metabolic rate of prostate cancer compared to other malignancies as well as the small size of the organ and proximity to the urinary bladder, into which most radiopharmaceuticals are eventually excreted. Accordingly, in some instances, the tissue region is the prostate gland.

A tumor is an abnormal mass of tissue as a result of abnormal growth or division of cells caused by cancer. Tumors can occur in a variety of different types of tissue such as the breast, lung, brain, liver kidney, colon, and prostate, can be malignant or benign, and generally vary in size from about 1 cm to about 5 cm.

The imaging methods of the disclosure are suitable for imaging any physiological process or disease in which PSMA is involved. Typically, imaging methods are suitable for identification of areas of tissues or targets which express high concentrations of PSMA. Typical applications include imaging malignant tumors or cancers that express PSMA, prostate cancer (including metastasized prostate cancer), and angiogenesis. Essentially all solid tumors express PSMA in the neovasculture. Therefore, the methods disclosed herein can be used to image nearly all solid tumors including lung, renal cell, glioblastoma, pancreas, bladder, sarcoma, melanoma, breast, colon, germ cell, pheochromocytoma, esophageal and stomach. Also, certain benign lesions and tissues including endometrium, schwannoma and Barrett's esophagus can be imaged according to the present disclosure. PSMA is frequently expressed in endothelial cells of capillary vessels in peritumoral and endotumoral areas of various malignancies such that compounds of the disclosure and methods of imaging using same are suitable for imaging such malignancies.

Cancer Treatment Using PSMA-Specific Agents

PSMA-specific agents can be used in a variety of different manners to carry out or assist in cancer treatment, for example, in prostate cancer treatment. In one aspect, the PSMA-specific agents are used to identify the location and/or severity of the cancer, after which the cancer is treated using a suitable method such as surgery or chemotherapy. In another aspect, the PSMA-specific agents are modified by replacing the imaging group with a toxin group so that the PSMA-specific agents become PSMA-specific anticancer agents. In yet another example, the same PSMA-specific agent can be used for imaging and therapy, utilizing the same or different radioisotope(s), by administering a therapeutically effective dose (which is typically higher than a detectably effective dose) to a patient in need thereof.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells", that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer.

In some instances, the method further includes the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

In some instances, PSMA-specific anticancer agents in which the imaging group has been replaced with a toxin are used to treat prostate cancer. In other instances, the PSMA-specific anticancer agents are used to treat metastatic cancer which has spread to one or more sites beyond the initial point where cancer has occurred. As noted herein, because PSMA occurs in a variety of different types of cancer, the PSMA-specific anticancer agents can be used to treat cancer other than prostate cancer.

Accordingly, in one aspect, the disclosure provides methods of treating tumors by administering to a subject a therapeutically effective amount of a PSMA-specific anticancer agent comprising a therapeutically effective toxin such as a radioisotope. In certain aspects, the tumor cells may express PSMA, such as prostate tumor cells or metastasized prostate tumor cells. In other examples, a tumor may be treated by targeting adjacent or nearby cells which express PSMA. For example, vascular cells undergoing angiogenesis associated with a tumor may be targeted. Essentially all solid tumors express PSMA in the neovasculature. Therefore, the methods described here can be used to image and treat nearly all solid tumors including lung, renal cell, glioblastoma, pancreas, bladder, sarcoma, melanoma, breast, colon, germ cell, pheochromocytoma, esophageal and stomach. Also, certain benign lesions and tissues including endometrium, schwannoma and Barrett's esophagus can be treated according to the present disclosure. Examples of therapeutically effective radioisotopes include $^{64}$Cu, $^{131}$I and $^{211}$At.

In some instances, the step ablating the cancer includes administering a therapeutically effective amount of an anticancer agent to the subject, which may be administered concurrently with or subsequent to treatment with the agents of the disclosure. Examples of anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-amino-1,2,4-benzotriazine 1,4-dioxide, aminopterin, cytosine β-D-arabinofuranoside, 5-fluoro-5'-deoxyuridine, 5-fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S (+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, gene regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; microtubule inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-amino-1,8-naphthalimide, apigenin, brefeldin A, cimetidine, dichloromethylene-diphosphonic acid, leuprolide, luteinizing-hormone-releasing hormone, pifithrin, rapamycin, thapsigargin, and bikunin.

Another method of ablating cancer such as prostate cancer that has been detected using a PSMA-specific agent is to conducting surgery to remove the cancer tissue (e.g., prostate cancer tissue) from the subject. The main type of surgery for prostate cancer is known as a radical prostatectomy. Radical prostatectomy involves removing the entire prostate gland plus some of the tissue around it, including the seminal vesicles. Examples of types of radical prostatectomy include radical retropubic prostatectomy, radical perineal prostatectomy, and laparoscopic radical prostatectomy.

In some instances, the surgery used to remove the cancer is robotic surgery that is guided by use of an imaging agent, for example, the PSMA-specific agent. For example, the robotic surgery can be near-infrared fluorescence-guided robotic surgery. One type of robotic surgery is robotic-assisted laparoscopic radical prostatectomy (RALRP). A robotic surgery system for performing robotic surgery with a surgery robot using guiding images of a part to be operated on, the robotic surgery system comprising: an endoscope apparatus for capturing medical images of a predetermined organ in a body to be examined; a non-endoscopic apparatus including at least one of an ultrasound apparatus, a computed tomography (CT) apparatus, a magnetic resonance imaging (MRI) apparatus, and a positron emission tomography (PET) apparatus for capturing medical images of the predetermined organ; a medical image processing apparatus for acquiring the medical images captured using the plurality of multi-modal medical image capturing apparatuses, extracting surface information of the predetermined organ, which is included in each of the medical images, from each of the medical images, mapping each of the medical images using the extracted surface information, and generating a synthesis image in which the medical images have been registered, based on the mapping result; a display apparatus for displaying the generated synthesis image; and the surgery robot for performing a robotic surgery. See for example US Patent Publications 2013/0035583 and 2013/0211420, the disclosures of which are incorporated herein by reference.

Administration and Formulation of PSMA-Specific Imaging and Anticancer Agents

In some instances, the PSMA-specific agent is administered in a pharmaceutically acceptable carrier, e.g., an aqueous carrier. A variety of carriers can be used, e.g., buffered saline and the like. These solutions are sterile and generally free of undesirable matter. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these Formulations can vary widely, and will be selected primarily based on fluid volumes, viscosities, body weight and the like in accordance with the particular mode of administration and imaging modality selected.

Administration of the PSMA-specific agent for in vivo imaging of a tissue, an organ or a full body can include a) providing a pharmaceutical Formulation comprising the imaging agent of the disclosure and, optionally, one or more pharmaceutically acceptable excipients, wherein the imaging agent is formed in any manner, including those described herein, and wherein the Formulation is suitable for administration as a PSMA-specific agent and the imaging agent is present in a detectably effective amount; b) providing an imaging device (i.e., an optical imaging device); c) administering the pharmaceutical Formulation in an amount sufficient to generate the tissue or body image; and d) imaging the distribution of the pharmaceutical Formulation of step a) with the imaging device, thereby imaging the tissue, organ or body.

Administration of the PSMA-specific agent for therapeutic purposes for the treatment of a cancer can include a) providing a pharmaceutical Formulation comprising the agent of the disclosure and, optionally, one or more pharmaceutically acceptable excipients, wherein the imaging agent is formed in any manner, including those described herein, and wherein the Formulation is suitable for administration as a PSMA-specific therapeutic agent and the imaging agent is present in a therapeutically effective amount. In one example, the PSMA-specific agent includes a radionuclide used for radiotherapy, such as $^{64}$Cu, $^{131}$I and $^{211}$At. Agents administered for therapeutic purposes will usually be administered via intravenous infusion or injection.

The pharmaceutical formulations described herein can be administered in a variety of unit dosage forms, depending upon the particular tissue or cancer to be imaged, the general medical condition of each patient, the method of administration, and the like. Details on dosages are well described in the scientific and patent literature. The exact amount and concentration of PSMA-specific agent or pharmaceutical of the disclosure and the amount of Formulation in a given dose, or the detectably/therapeutically effective dose can be routinely determined by, e.g. the clinician. The dosing regimen will depend upon a variety of factors, e.g. whether the tissue region or tumor to be imaged or treated is disseminated or local, the general state of the patient's health, age and the like.

The pharmaceutical compositions disclosed herein can be delivered by any means known in the art systematically (e.g. intravenously), regionally or locally (e.g. intra- or peritumoral or intracystic injection, e.g. to image bladder cancer) by e.g. intraarterial, intratumoral, intravenous (iv), parenteral, intrapleural cavity, topical, oral or local administration, as subcutaneous intra-zacheral (e.g. by aerosol) or transmucosal (e.g. voccal, bladder, vaginal, uterine, rectal, nasal, mucosal), intra-tumoral (e.g. transdermal application or local injection). For example, intra-arterial injections can be used to have a "regional effect", e.g. to focus on a specific organ (e.g. brain, liver, spleen, lungs).

Preparation of the Compounds

PSMA-specific agents may be synthesized by synthetic routes that include processes similar to those well known in the chemical arts, particularly in light of the description contained herein. The starting materials are generally available from commercial sources such as Aldrich Chemicals (Milwaukee, Wisconsin, USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie,* 4, Aufl. Ed. Springer-Verlag, Berlin, Germany, including supplements (also available via the Beilstein online database)).

Those skilled in the art will appreciate that synthetic routes other than those described in the examples herein may be used to synthesize the compounds of the disclosure. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present disclosure is illustrated by the following examples. It is to be understood that the particular examples, materials, amounts, and procedures are to be interpreted broadly in accordance with the scope and spirit of the disclosure as set forth herein.

EXAMPLES

Example 1—Compound Synthesis

Compound 1: DOTA-JB330 (JB1498)

Compound 1 was synthesized by performing seven standard cycles of Fmoc-peptide synthesis using a Rink amide resin (Peptides International) as detailed below. At the beginning of each coupling cycle, the Fmoc was removed with 20% piperidine in DMF (Alfa Aesar).

1. Fmoc-Lys (DOTA-tBu$_3$)-OH (100 mg) (Macrocylics) was reacted with 0.40 g of Rink amide resin (0.45 mmol/g or 0.18 meq), followed by a capping with 1.4 mL DMF+40 microliter of glacial acetic acid (EMD-Millipore), 0.25 g of HCTU (Novabiochem) and 173 microliter of DIPEA (Sigma-Aldrich).

2. Fmoc-Tyr (tBu)-OH (0.182 g) (Bachem)+376 microliter HCTU (0.467 g dissolved in 1.13 mL DMF)+104 microliter DIPEA 3. Fmoc-D-Glu (OtBu)-OH (0.168 g) (Peptides International)+376 microliter HCTU (0.467 g dissolved in 1.13 mL DMF)+104 microliter DIPEA 4. Fmoc-D-Glu (OtBu)-OH (0.168 g)+376 microliter HCTU (0.467 g dissolve in 1.13 mL DMF)+104 microliter DIPEA 5. Fmoc-D-Glu (OtBu)-OH (0.168 g)+376 microliter HCTU (0.467 g dissolve in 1.13 mL DMF)+104 microliter DIPEA 6. Fmoc-Ahx-OH (0.140 g) (Peptides International)+376 microliter HCTU (0.467 g dissolved in 1.13 mL DMF)+104 microliter DIPEA 7. (Fmoc-Glu-OtBu (0.168 g)+376 microliter HCTU (0.467 g dissolved in 1.13 mL DMF)+104 microliter DIPEA The last amino acid was coupled through the N-terminal urea using 5 molar equivalents of isocyanate derivative of di-t-butyl ester of glutamate.

Fmoc was removed with 20% piperidine (Aldrich) in DMF followed by DMF washing.

The resin was washed with dichloromethane (Fisher Chemical) and remained soaking in dichloromethane until ready for reaction with isocyanate.

Isocyanate formation: A solution of 0.151 g of H-Glu (OtBu)-OtBu (Bachem) in 1 mL dichloromethane+223 microliter of DIPEA was added dropwise on dry ice to a solution of 0.0456 g of triphosgene (Chem-Impex International) in 1 mL dichloromethane.

Reacting the isocyante with the N-terminus of the peptide chain on the resin: Allow the isocyanate solution to warm to room temperature. After 30 min at room temperature, 112 microliter DIPEA was added to the solution. The mixture was poured onto resin and incubated at room temperature for 1 h. The resin was washed with DCM, DMF and methanol.

Cleavage and Deprotection: 5.0 mL of a cleavage mixture using TFA (EMD Millipore)/TIS (Aldrich)/$H_2O$ (95%/2.5%/2.5%) was reacted with resin for 4 h at room temperature. The cleavage mixture was collected and TFA was evaporated with a stream of air. The residual liquid was precipitated with diethyl ether (Sigma-Aldrich) to afford 170 mg of a solid crude product that was collected and air dried. The crude product was washed with diethyl ether. The solid was recollected and dried in air and under vacuum.

The final product was purified via HPLC (Column: Symmetry C18 (Waters) 4.6×150 mm analytical column) using the following solvent system: A: water with 0.1% formic acid; B: acetonitrile (J. T. Baker), using a gradient of 10% B to 14% B over 10 minutes (flow rate: 1.0 ml/min). The desired product elutes at 10.4 min under the provided conditions. The HPLC purified product was lyophilized and dissolved in 800 microliters of Ultrapure water (EMD Millipore) to provide Compound 1. The purified Compound 1 was determined to be more than 95% pure (HPLC) and LC-MS demonstrates m/z=1497.7 by mass spectroscopy.

Compound I was successfully chelated with cold gallium (heating with $Ga(NO_3)_3$, m/z=1565), as well as Lu (heating with $LuCl_3$, m/z=1670). Compound 1 was further chelated with $^{68}Ga$ using $^{68}GaCl_3$.

Compound 2: DOTA-JB-1664

Compound 2 was synthesized with standard Fmoc peptide synthesis to produce E'EC6EEEYK with an N-terminal urea as reported in Kozikowski et al. After HPLC purification and lyophilization, the peptide was reacted with the bifunctional chelate isothiocyanatobenzyl-DOTA (SCN-Bn-DOTA) to form Compound 2.

The HPLC (C18) profile of purified Bn-DOTA chelate exhibited a single peak with retention time of 10.7 min. LC-MS of the peak demonstrated chelation with the most abundant natural isotope with a m/z=1664.

Compound 2 was labeled with $^{nat}Ga$. HPLC (C18) exhibited two peaks having retention times of 11.2 and 12.2 minutes. Mass spectroscopy showed both peaks to have the exact same mass, with the most abundant isotope form having m/z=1731.

Compound 2 was successfully radiolabeled with $^{68}Ga$.

Compound 3: E'KC4EEEC6 (6-fluoro-pyridine-3-carbonyl)

Compound 3 was synthesized starting with Fmoc-Lys (Mtt)-Wang resin. The Fmoc protecting group was removed with 20% piperidine, the product washed with DMF and then washed with DCM. N-glu (OtBu)-OtBu was treated with triphosgene and DIEA in DCM (−78° C. brought to room temp). The product was added to resin with DIEA (di-isopropyl-ethyl-amine). The sidechain protecting Mtt group was selectively removed with 1% TFA in DCM or DCM/HFIP/TFE/TES (6.5:2:1:0.5). The resulting product was washed with DMF and 20% piperidine, followed by washing with DMF. Standard peptide synthesis was continued in the following order: Fmoc-GABA-OH, Fmoc-D-Glu (OtBu)-OH, Fmoc-D-Glu (OtBu)-OH, Fmoc-D-Glu (OtBu)-OH, Fmoc-6-Ahx-OH, 6-fluoro-nicotinic acid. Deprotection and cleavage yielded E'KC4EEEK (6-fluoro-pyridine-3-carbonyl).

If (N,N,N-trimethyl-5-((2,3,5,6-tetrafluorophenoxy)-carbonyl) pyridin-2-aminium trifluoromethanesulfonate) was used for the last step, the reaction would yield E'KC4EEEK (6-(trimethylamino)pyridin-3-carbonyl).

Compound 4: E'KC4EEEC6 (6-fluoro-pyridine-3-carbonyl)-DOTA

Compound 4 was synthesized starting with Fmoc-Lys (Mtt)-Wang resin. The Fmoc protecting group was removed with 20% piperidine, the product washed with DMF and then washed with DCM. N-glu (OtBu)-OtBu was treated with triphosgene and DIEA in DCM (−78° C. brought to room temp). The product was added to resin with DIEA (di-isopropyl-ethyl-amine). The sidechain protecting Mtt group was selectively removed with 1% TFA in DCM or DCM/HFIP/TFE/TES (6.5:2:1:0.5). The resulting product was washed with DMF and 20% piperidine, followed by washing with DMF. Standard peptide synthesis was continued in the following order: Fmoc-GABA-OH, Fmoc-D-Glu (OtBu)-OH, Fmoc-D-Glu (OtBu)-OH, Fmoc-D-Glu (OtBu)-OH, Fmoc-Ahx-OH, Fmoc-Lys (Mtt)-OH. The sidechain protecting Mtt group was selectively removed with 1% TFA in DCM or DCM/HFIP/TFE/TES (6.5:2:1:0.5). 6-Fluoro-nicotinic acid was coupled to the peptide chain and deprotection and cleavage yields E'KC4EEEK (6-Fluoro-pyridine-3-carbonyl).

If (N,N,N-trimethyl-5-((2,3,5,6-tetrafluorophenoxy)-carbonyl) pyridin-2-aminium trifluoromethanesulfonate) was used for the last step, the reaction would yield E'KC4EEEK (6-(trimethylamino)pyridin-3-carbonyl).

Compound 5: E'KC4EEEC6 (Cy)-DOTA See method for Compound 4.

Compound 6: E'KC4EEEC6 (6-FAM)-DOTA

See method for Compound 4.

Compound 7: E'K-E-(6-fluoro-pyridine-3-carbonyl)

Compound 7 was synthesized starting with Fmoc-Lys (Mtt)-Wang resin. The Fmoc protecting group was removed with 20% piperidine, the product washed with DMF and then washed with DCM. N-glu (OtBu)-OtBu was treated with triphosgene and TEA in DCM (−78° C. brought to room temp). The product was added to resin with DIEA (di-isopropyl-ethyl-amine). The sidechain protecting Mtt group was selectively removed with 1% TFA in DCM or DCM/HFIP/TFE/TES (6.5:2:1:0.5). The resulting product was washed with DMF and 20% piperidine, followed by washing with DMF. Standard peptide synthesis was continued in the following order: Fmoc-D-Glu (OtBu)-OH (1×, 2× or 3×), 6-fluoro-nicotinic acid. Deprotection and cleavage yielded E'K-E-(6-fluoro-pyridine-3-carbonyl).

If (N,N,N-trimethyl-5-((2,3,5,6-tetrafluorophenoxy)-carbonyl) pyridin-2-aminium trifluoromethanesulfonate) was used for the last step, the reaction would yield E'K-E-(6-(trimethylamino)pyridin-3-carbonyl).

Compound 8 See method for compound 7.

Compound 10

Compound 10 was synthesized starting with Fmoc-Lys (Mtt)-Wang resin. The Fmoc protecting group was removed with 20% piperidine, the product washed with DMF and then washed with DCM. N-glu (OtBu)-OtBu was treated with triphosgene and DIEA in DCM (−78° C. brought to room temp). The product was added to resin with DIEA (di-isopropyl-ethyl-amine). The sidechain protecting Mtt group was selectively removed with 1% TFA in DCM or DCM/HFIP/TFE/TES (6.5:2:1:0.5). The resulting product was washed with DMF and 20% piperidine, followed by washing with DMF. Standard peptide synthesis was continued in the following order: Fmoc-D-Glu (OtBu)-OH, Fmoc-D-Glu (OtBu)-OH, Fmoc-GABA-OH. Deprotection and cleavage yielded Compound 10. The purified Compound 10 demonstrated m/z=1049 by mass spectroscopy.

Compound 10 was successfully chelated with cold gallium (heating with $Ga(NO_3)_3$, m/z=1117), as well as 68Ga with radiochemical purity of over 90%. Compound 10 was also chelated with cold yttrium (m/z=1135) and lutecium (m/z=1221).

Compound 11

Compound 11 was synthesized starting with Fmoc-Lys (Mtt)-Wang resin. The Fmoc protecting group was removed with 20% piperidine, the product washed with DMF and then washed with DCM. N-glu (OtBu)-OtBu was treated with triphosgene and DIEA in DCM (−78° C. brought to room temp). The product was added to resin with DIEA (di-isopropyl-ethyl-amine). The sidechain protecting Mtt group was selectively removed with 1% TFA in DCM or DCM/HFIP/TFE/TES (6.5:2:1:0.5). The resulting product was washed with DMF and 20% piperidine, followed by washing with DMF. Standard peptide synthesis was continued in the following order: Fmoc-D-Glu (OtBu)-OH, Fmoc-D-Glu (OtBu)-OH, 6-fluoro-nicotinic acid. Deprotection and cleavage yielded the Compound 11 precursor. The Compound 11 precursor demonstrated m/z=740 by mass spectroscopy.

The precursor was successfully fluorinated to form Compound 11 (m/z=701).

Radiofluorination of Compound 11 to synthesize $^{18}F$-labelled Compound 11

Radiofluorination was accomplished with 18F-fluoride using 0.5 mg of the Compound 11 precursor in 50% acetonitrile/DMSO missed with azeotropically dried $^{18}F$-tetraethylammonium fluoride. The mixture was incubated at 80° C. for 10 min, diluted with water before loading onto a Sep-Pak C18 cartridge and eluting with 20% ethanol. HPLC with 5-50% acetonitrile showed a peak with corresponding radio peak eluting between 10.5 and 11 minutes.

Compound 12

Compound 12 was synthesized starting with Fmoc-Lys (Mtt)-Wang resin. The Fmoc protecting group was removed with 20% piperidine, the product washed with DMF and then washed with DCM. N-Glu (OtBu)-OtBu was treated with triphosgene and DIEA in DCM (−78° C. brought to room temp). The product was added to resin with DIEA (di-isopropyl-ethyl-amine). The sidechain protecting Mtt group was selectively removed with 1% TFA in DCM or DCM/HFIP/TFE/TES (6.5:2:1:0.5). The resulting product was washed with DMF and 20% piperidine, followed by washing with DMF. Standard peptide synthesis was continued in the following order: Fmoc-D-Glu (OtBu)-OH, Fmoc-D-Glu (OtBu)-OH, Fmoc-GABA-OH.

The resulting product was suspended in 3 molar equivalents of (N,N,N-trimethyl-5-((2,3,5,6-tetrafluorophenoxy)-carbonyl) pyridin-2-aminium chloride) in DMF and DIEA and mixed with the resin for 2 h or until a ninhydrin test of the resin is negative to afford Compound 12 (m/z 701).

Compound 14 (E'K-E!E!Y-DOTA)

Compound 14 was synthesized starting with Fmoc-Lys (Mtt)-Wang resin. The Fmoc protecting group was removed with 20% piperidine, the product washed with DMF and then washed with DCM. N-Glu (OtBu)-OtBu was treated with triphosgene and DIEA in DCM (−78° C. brought to room temp). The product was added to resin with DIEA (di-isopropyl-ethyl-amine). The sidechain protecting Mtt group was selectively removed with 1% TFA in DCM or DCM/HFIP/TFE/TES (6.5:2:1:0.5). The resulting product was washed with DMF and 20% piperidine, followed by washing with DMF. Standard peptide synthesis was continued in the following order: Fmoc-D-Glu (OtBu)-OH, Fmoc-D-Glu (OtBu)-OH, Fmoc-Tyr (tBu)-OH, DOTA-tris (tBu ester). Compound 14 demonstrated m/z=1127 by mass spectroscopy.

Incubation of Compound 14 with gallium nitrate in water at 97° C. resulted in the complexed product having m/z=1196.

Compound 15 (E'K-C4EEEC4-FITC)

Compound 15 was synthesized starting with Fmoc-Lys (Mtt)-Wang resin. The Fmoc protecting group was removed with 20% piperidine, the product washed with DMF and then washed with DCM. N-Glu (OtBu)-OtBu was treated with triphosgene and DIEA in DCM (−78° C. brought to room temp). The product was added to resin with DIEA (di-isopropyl-ethyl-amine). The sidechain protecting Mtt group was selectively removed with 1% TFA in DCM or DCM/HFIP/TFE/TES (6.5:2:1:0.5). The resulting product was washed with DMF and 20% piperidine, followed by washing with DMF. Standard peptide synthesis was continued in the following order: Fmoc-GABA-OH, Fmoc-Glu (OtBu)-OH, Fmoc-Glu (OtBu)-OH, Fmoc-Glu (OtBu)-OH, Fmoc-GABA-OH, fluorescein isothiocyanate.

Compound 16 (E'K-C4EEE-C4-DOTA)

Compound 16 was synthesized starting with Fmoc-Lys (Mtt)-Wang resin. The Fmoc protecting group was removed with 20% piperidine, the product washed with DMF and then washed with DCM. N-Glu (OtBu)-OtBu was treated with triphosgene and DIEA in DCM (−78° C. brought to room temp). The product was added to resin with DIEA (di-isopropyl-ethyl-amine). The sidechain protecting Mtt group was selectively removed with 1% TFA in DCM or DCM/HFIP/TFE/TES (6.5:2:1:0.5). The resulting product was washed with DMF and 20% piperidine, followed by washing with DMF. Standard peptide synthesis was continued in the following order: Fmoc-Glu (OtBu)-OH, Fmoc-Glu (OtBu)-OH, Fmoc-GABA-OH, DOTA-tris (tBu ester). Compound 14 demonstrated m/z=1264 and 632 by mass spectroscopy.

Incubation of Compound 16 with lutetium chloride in water at 97° C. resulted in the complexed product having m/z=1435 and 730 by mass spectroscopy.

Example 2—Competitive Binding Assay

PC3-PIP PSMA-expressing cells were grown to confluency, harvested in 50 mM Tris-HCl (pH 7.5) and subjected to four freeze/thaw cycles. Cell membranes were washed three times by centrifugation at 12,000g or higher. The cell membranes were diluted to 50 mg/mL in 50 mM Tris-HCl (pH 7.5) (based on wet weight of the solid after centrifugation). Binding assays were conducted in 96 well plates. Phase 1 of the assay used wells containing 100 microliters 50 mM Tris-HCl (pH 7.5) with 4 microns NAAG and 10 microns of PC3-PIP membrane, to which differing concentrations of Compound 1 was added. The 96 well plate was incubated at 37° C. for 2 h. The glutamic acid concentration was measured with the Amplex Red glutamic acid assay kit (Invitrogen-Molecular Probes) using a fluorescent plate reader (530 nm excitation, 590 nm emission). The resulting fluorescence signals were normalized, and normalized fluorescence plotted against the concentration of ligand (log (nm)) (FIG. 1). EC50 was determined according to Eq. 1 (below).

$$\text{fluorescene} = \text{baseline fluorscence} + (\text{max fluorscene} - \text{baseline}) * \left[1 + \frac{1}{\left(\frac{EC50}{\text{ligand concentration}}\right)}\right]$$

Figure 2:
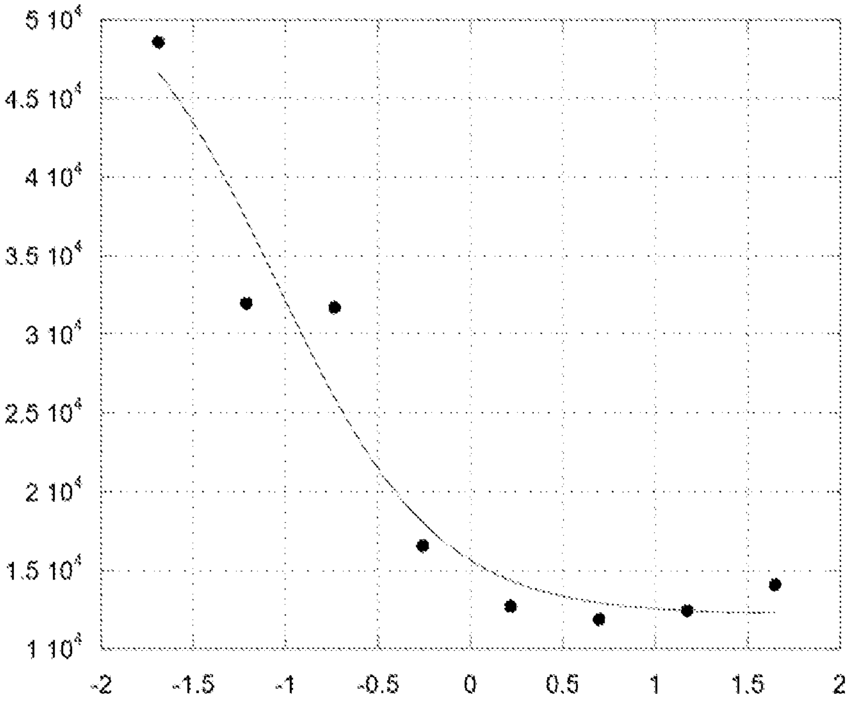
FIG. 2 provides the results of a competitive binding assay for Compound 1 in PC3-PIP PSMA-expressing cells (x-axis: concentration of Compound 11 (log (nm); y-axis: fluorescence).
Figure 3:
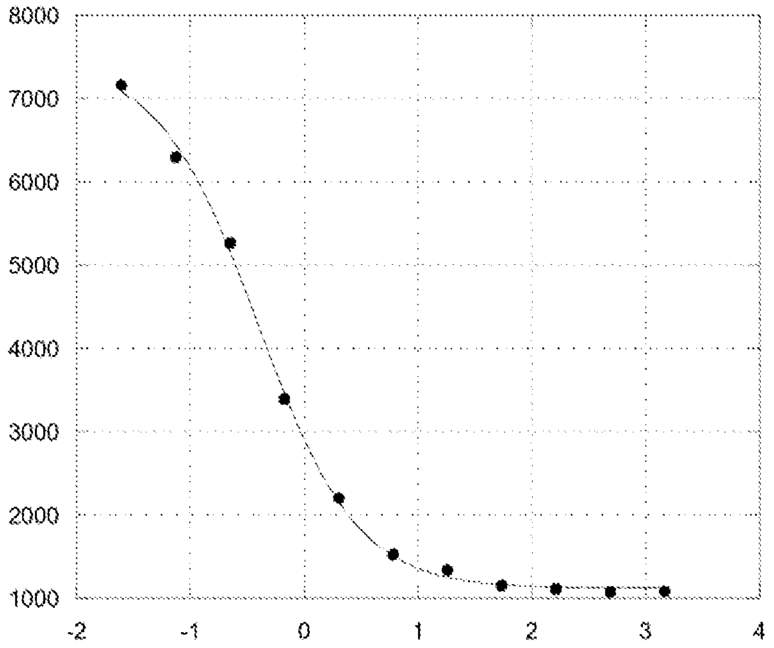
FIG. 3 provides the results of a competitive binding assay for Compound 1 in PC3-PIP PSMA-expressing cells (x-axis: concentration of Compound 14 (log (nm); y-axis: fluorescence).

As seen in FIG. 1 (x-axis: concentration of Compound 1; y-axis: fluorescence), the EC50 value for Compound 1 was estimated to be 287±64 pm. An estimated $K_i$ for Compound 1 to PSMA was calculated to be better than 300 pM. FIG. 2 (x-axis: concentration of Compound 11; y-axis: fluorescence) demonstrates that the EC50 value for Compound 11 was estimated to be around 0.1 nM. FIG. 3 (x-axis: concentration of Compound 14; y-axis: fluorescence) demonstrates that the EC50 value for Compound 14 binding to PSMA was determined to be 0.39±0.02 nM.

Example 3—Flow Cytometry

Figure 4A:
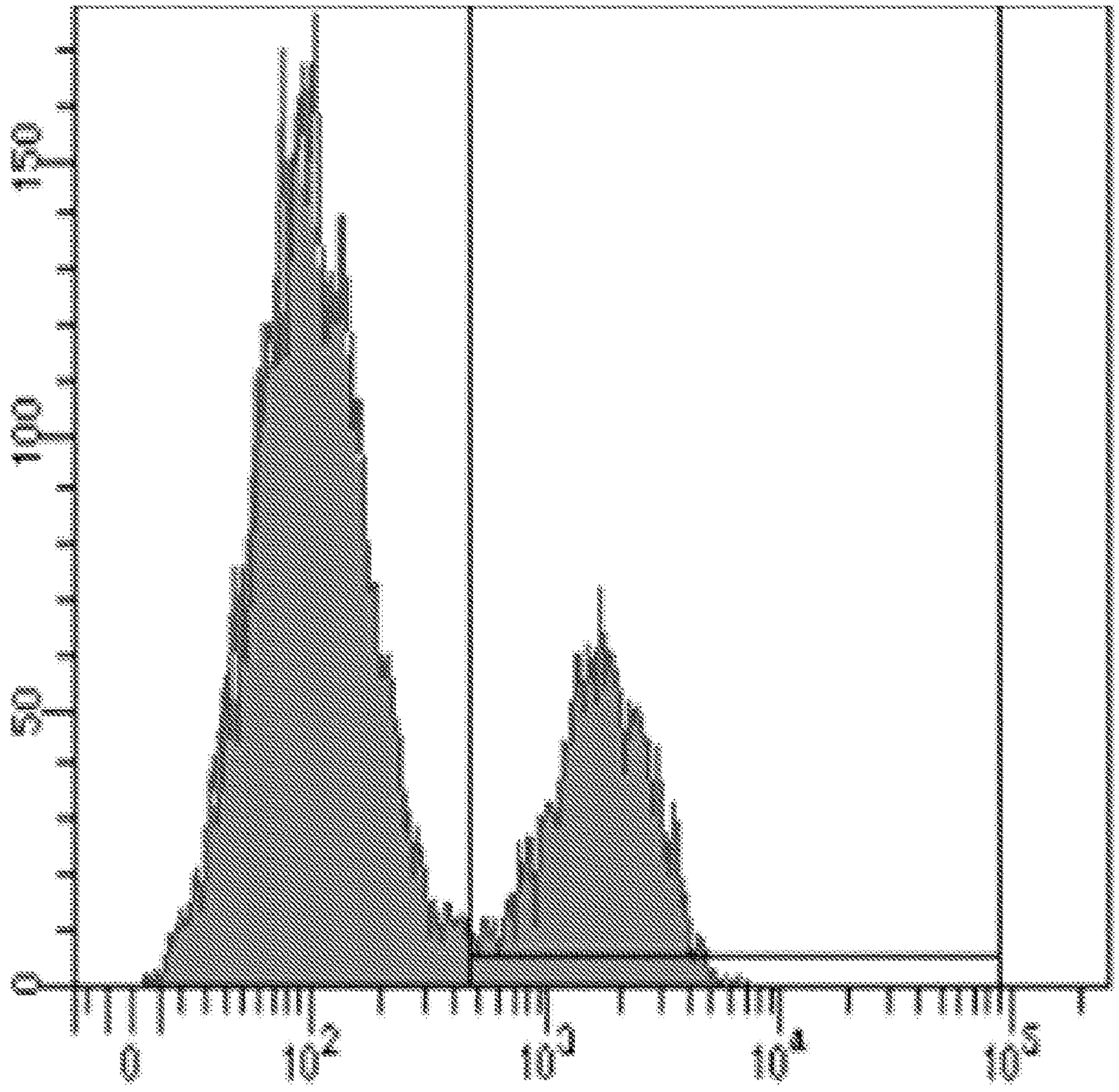
FIG. 4 shows the results of a flow cytometry study with Compound 12 at 14 nm (FIG. 4A) and 2 nM (FIG. 4B) in PC3-PIP PSMA-expressing cells.
FIG. 4C is a histogram of unlabeled PC3-PIP cells.
Figure 4B:
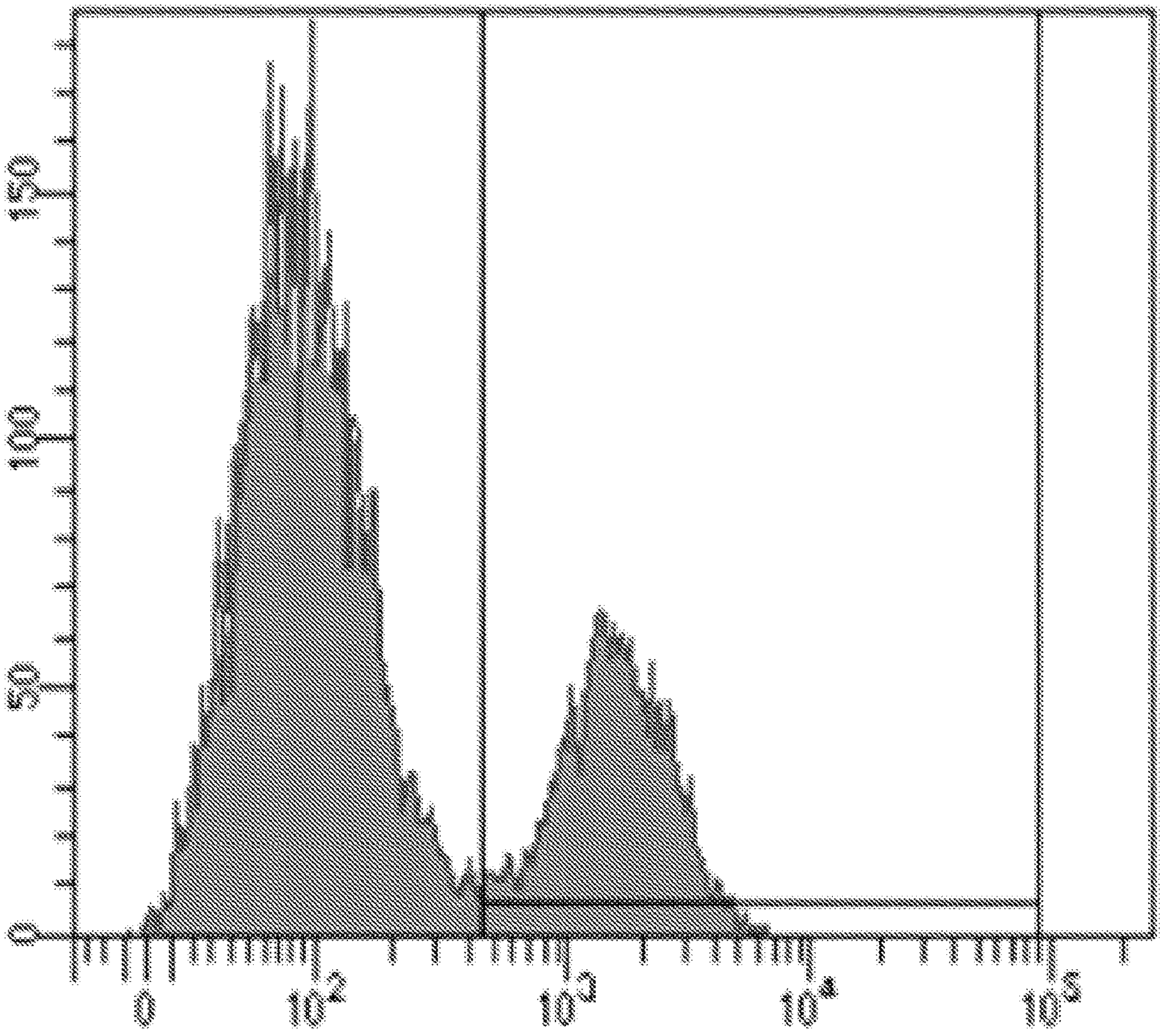
Figure 4C:
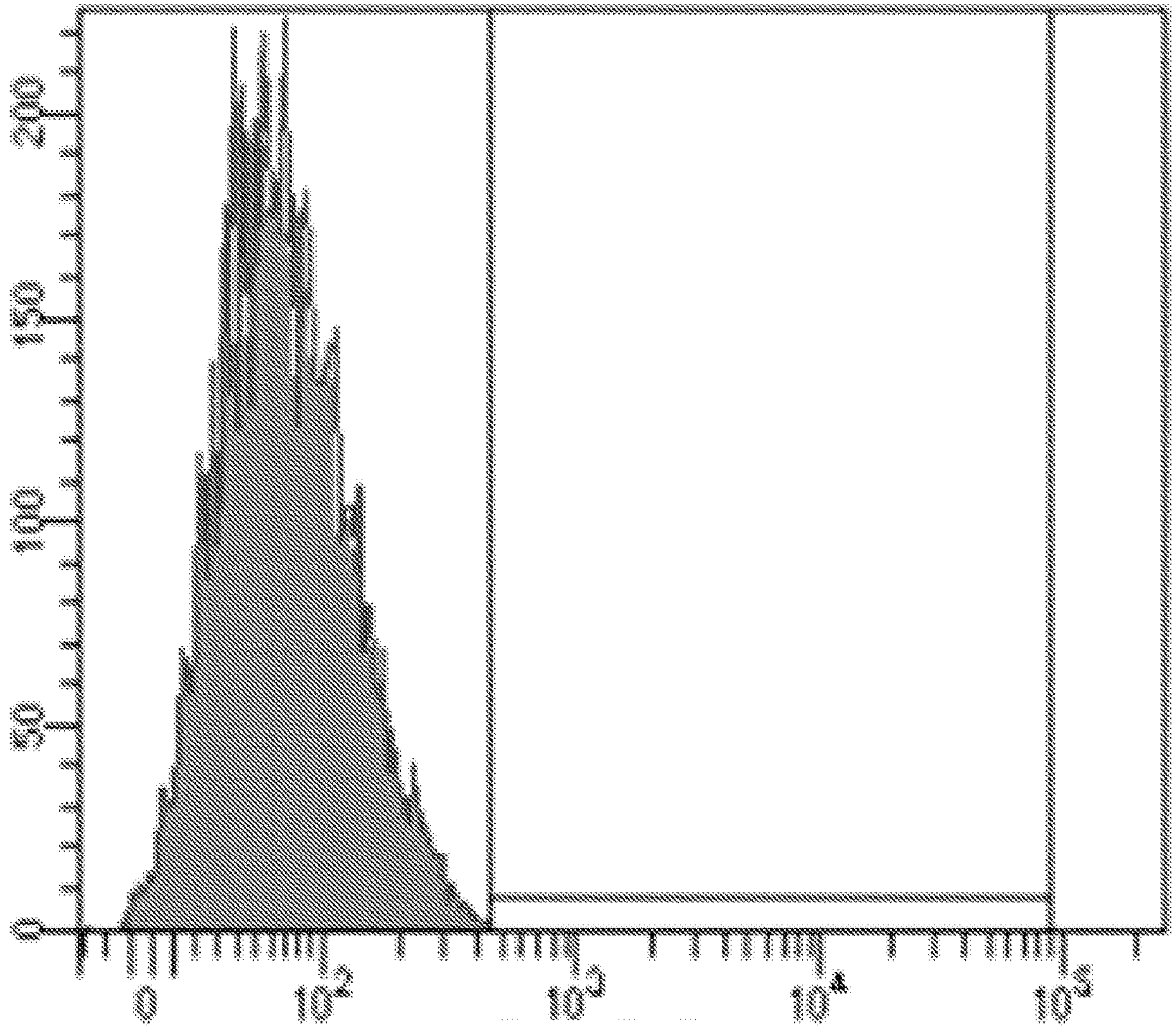

PC3-PIP cells were incubated with Compound 12 at 14 nM (FIG. 4A) or 2 nM (FIG. 4B) concentrations on ice. The histograms of FIG. 4 demonstrate that the PC3-PIP cell line is a mixture of PSMA-expressing cells and PSMA-nonexpressing cells. There is specific binding of Compound 12 to cells with PSMA expression. There is minimal difference in intensity histogram of cells incubated with 14 nM and 2 nM of Compound 12, indicating apparent Kd below 2 nM. The flow cytometry also revealed that only 25% of the PC3-PIP cells stock express PSMA. FIG. 4C is the histogram of un-labeled PC3-PIP cells.

Example 4—Biodistribution Study

Compound 1 was radiolabeled with $^{68}$Ga using 2.5 microliters of Compound 1 (2.4 mg/mL), 250 microliters of NaOAc buffer and 1.0 mL of ITG-$^{68}$Ga generator eluate (approximately 1 mCu/1 mL). The reaction was heated at 97° C. for 7 min. The aqueous solution was concentrated under vacuum with gentle heat for 10 min. The mixture was loaded onto HPLC and purified using a gradient of 9% to 35% acetonitrile in water with 0.1% formic acid, flow rate 1.5 mL/min, wherein the product peak eluted at 6.3 min. The eluant was purified from acetonitrile under vacuum. The residual formic acid in solution was buffered with 5 microliters of 1M NaOAc and 6 microliters of 1M NaOH, then diluted 1:1 with phosphate buffer saline (PBS). The final pH was 4.5.

Three NSG mice were inoculated subcutaneously with 4 million cells of PC3-PIP PSMA-expressing cells. Biodistribution studies were conducted once the long axis of the tumor was greater than 1 cm. Each mouse was injected with 100 microliters of the Compound 1 tracer solution under anesthesia via retro-orbital injection in the right eye and euthanized 1 hour after injection. The organs were dissected for radioactive quantitation.

As provided for in Table 3 below, the tumor and kidneys demonstrated the highest uptake of radioactivity. Given the known urinary uptake/clearance of similar compounds, the high level of activity in the kidney was not surprising. Compound 1 demonstrates otherwise high specify for PSMA-expressing tumor cells.

TABLE 3

| Organ | Biodistribution Compound 1 | Biodistribution AlF5 (AlF-NOTA-JB330) | Biodistribution PSMA 11 |
|---|---|---|---|
| Blood | 0.22% ± 0.02% | 0.18% ± 0.09% | 0.31% ± 0.08% |
| Muscle | 0.22% ± 0.23% | 0.19% ± 0.12% | 0.54% ± 0.14% |
| Bone | 0.11% ± 0.04% | 0.39% ± 0.28% | |
| Liver | 0.20% ± 0.09% | 0.41% ± 0.10% | 0.44% ± 0.13% |
| Kidney | 12.98% | 16.82% ± 5.6% | 182% ± 33% |
| Spleen | 0.31% ± 0.12% | 0.29% ± 0.14% | 22.2% ± 7.91% |
| Heart | 0.12% ± 0.01% | 0.14% ± 0.11% | |
| Lung | 0.24% ± 0.05% | 0.21% ± 0.05% | |
| Salivary Gland | 0.13% ± 0.01% | | 10.00% ± 2.52% |
| Tumor | 12.09% ± 1.28% | 6.91% ± 1.14% | 8.67% ± 1.97% |

Surprisingly, it was found that Compound 1 demonstrates improved specificity for PSMA-expressing tumor cells as compared to two related compounds. AlF5 was reported by Huang, et al. "Improving the Biodistribution of PSMA-Targeting Tracers with a Highly Negatively Charged Linker" The Prostate, 74 702-713 (2014) is identical in structure to Compound 2 of the present disclosure except it includes a NOTA imaging group rather than DOTA. As seen in Table 3, Compound 1 provides for higher tumor uptake and lower kidney uptake than does AlF5 (radiolabeled with $^{18}$F). Similarly, biodistribution studies for 68Ga-labelled PSMA-11 (Rousseau et al, "Monosodium Glutamate Reduces $^{68}$Ga-PSMA-11 (a.k.a Glu-NH—CO—NH-Lys (Ahx)-[$^{68}$Ga(HBEDCC]). Uptake in Salivary Glands and Kidneys in a Preclinical Prostate Cancer Model." J. Nucl. Med. 59 (12) 1865-1868 (2018)) show less relative tumor uptake compared to that of Compound 1. Further, PSMA-11 is well documented as resulting in high salivary gland uptake, which can be somewhat mitigated when co-administered with monosodium glutamate (as seen in Table 3). As indicated in Table 3, the salivary gland has only a minimal amount of uptake of Compound 1, around 0.1% and 1000-fold less than the observed tumor uptake. That provides a role for the compounds of the present disclosure as therapeutics, which is not feasible for prior art compounds given their significant non-specific uptake of untargeted organs.

Many variations and modifications may be made to the above-described embodiments of the disclosure without departing substantially from the spirit and various principles of the disclosure. All such modifications and variations are intended to be included herein within the scope of this disclosure and protected by the following claims.

What is claimed is:

1. A PSMA-specific agent or pharmaceutically acceptable salt thereof comprising a compound according to Formula II,

II

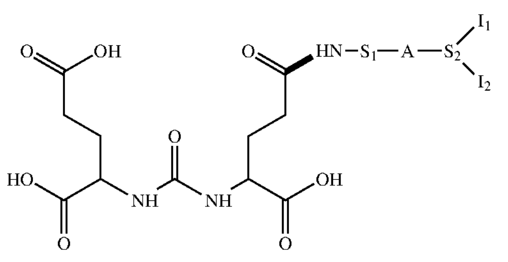

wherein $S_1$ is an organic spacer group of formula

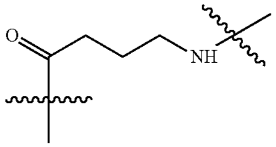

,

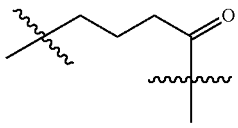

, or

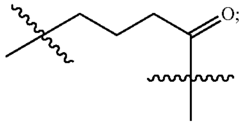

A is an amino acid chain comprising 2-5 amino acids and wherein at least two amino acids are Glu; $S_2$ is optionally present, and when present $S_2$ is an organic spacer selected from an aryl group or one of the following groups:

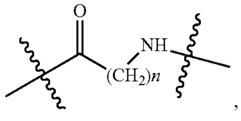

,

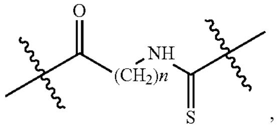

,

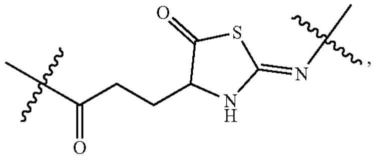

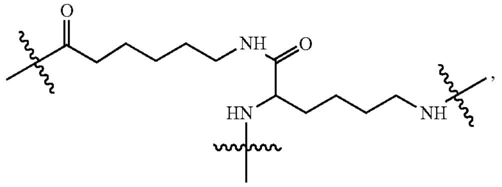

, or

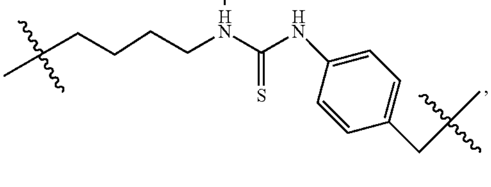

wherein n is from 3 to 5;

$I_1$ comprises DOTA; and $I_2$ is either absent or comprises and imaging group selected from one of the following groups:

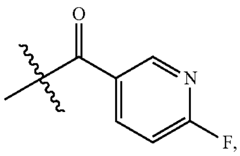

-continued

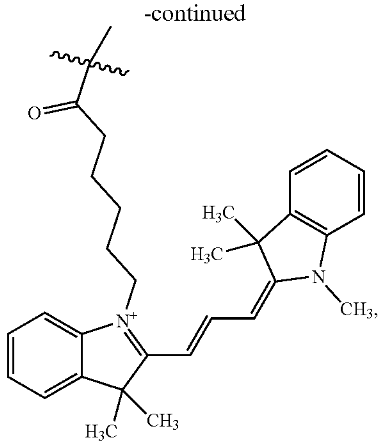

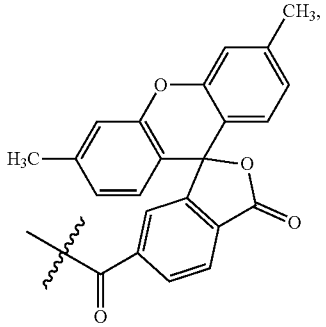

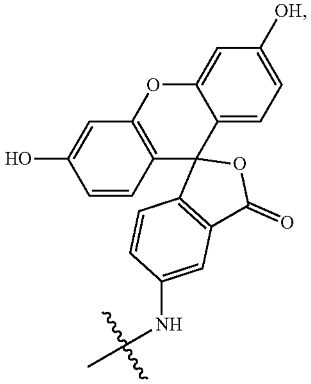

or

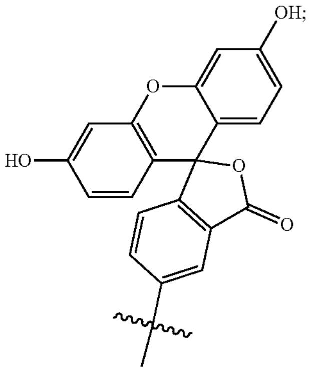

wherein each of $I_1$ and $I_2$ optionally contain a radioisotope.

2. The PSMA-specific agent of claim 1, wherein $S_1$ comprises an organic spacer comprising 5 carbons.

3. The PSMA-specific agent of claim 1, wherein A comprises an amino acid chain comprising 5 amino acids.

4. The PSMA-specific agent of claim 1, wherein A comprises an amino acid chain comprising Glu-Glu-Glu.

5. The PSMA-specific agent of claim 1, wherein A comprises an amino acid chain comprising Glu-Glu-Glu-Tyr.

6. The PSMA-specific agent of claim 1, wherein A comprises an amino acid chain comprising Lys.

7. The PSMA-specific agent of claim 1, wherein A comprises an amino acid chain comprising thiolysine.

8. The PSMA-specific agent of claim 1, wherein A is an amino acid chain consisting of Glu-Glu-Glu-Tyr-Lys.

9. The PSMA-specific agent of claim 1, wherein A is an amino acid chain consisting of Glu-Glu-Glu-Tyr-thioLys.

10. The PSMA-specific agent of claim 1, wherein $S_2$ is present and is an organic spacer comprising an aryl group.

11. The PSMA-specific imaging agent of claim 1, wherein $I_2$ is absent.

12. The PSMA-specific imaging agent of claim 1, wherein $S_2$ is absent.

13. The PSMA-specific agent of claim 1 having the following Formula:

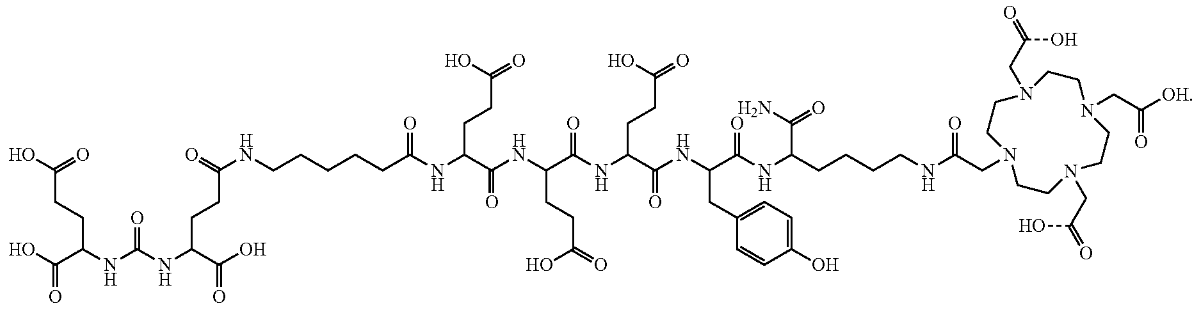

14. The PSMA-specific agent of claim 1 having the following Formula:

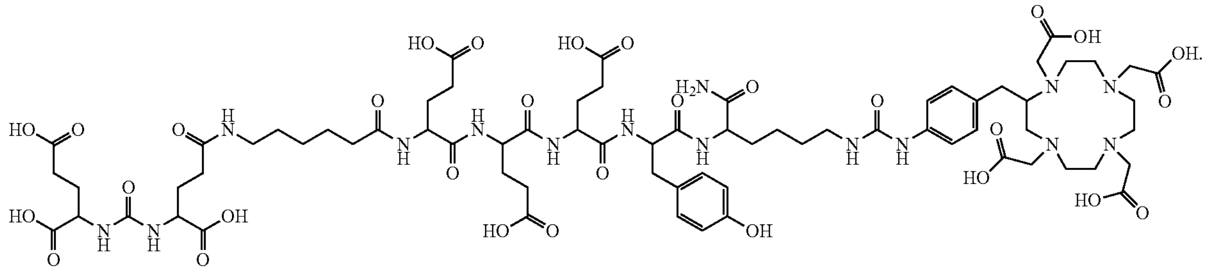 [SMILES: NC(=O)C(CCCCNC(=O)Nc1ccc(CC2CN(CC(=O)O)CCN(CC(=O)O)CCN(CC(=O)O)CCN2CC(=O)O)cc1)NC(=O)C(Cc1ccc(O)cc1)NC(=O)C(CCC(=O)O)NC(=O)C(CCC(=O)O)NC(=O)C(CCC(=O)O)NC(=O)CCCCCNC(=O)CCC(NC(=O)NC(CCC(=O)O)C(=O)O)C(=O)O]

15. The PSMA-specific agent of claim 1, wherein $I_1$ and/or $I_2$ are radiolabeled.

16. A method of imaging a cancer cell, comprising administering to a patient the PSMA-specific agent of claim 1 and monitoring an imaging output from the agent.

17. The method of claim 16, wherein the PSMA-specific agent comprises a PET or SPECT imaging radionuclide.

18. The method of claim 17, wherein the radionuclide is selected from the group consisting of a radioactive isotope of Cu, Tc, F, Ga, Lu, Y, Sm, Lu, At, Tb, Zr, Sc, and Ac.

19. The method of claim 16, wherein the imaging is PET imaging.

20. A method of treating a cancer, comprising administering to a patient in need thereof a PSMA-specific agent of claim 1.

21. The method of claim 20, wherein the PSMA-specific agent also acts as an imaging agent.

* * * * *